US010829519B2

(12) United States Patent
Gallagher et al.

(10) Patent No.: US 10,829,519 B2
(45) Date of Patent: Nov. 10, 2020

(54) ANGIOTENSIN (1-7) ANALOGS AND METHODS RELATING THERETO

(71) Applicants: WAKE FOREST UNIVERSITY HEALTH SCIENCES, Winston-Salem, NC (US); TENSIVE CONTROLS, INC., Colombia, MO (US)

(72) Inventors: Patricia Gallagher, Lewisville, NC (US); Ann Tallant, Lewisville, NC (US); Daniel Yohannes, Winston-Salem, NC (US); Kenneth A. Gruber, Columbia, MO (US)

(73) Assignees: WAKE FOREST UNIVERSITY HEALTH SCIENCES, Winston-Salem, NC (US); TENSIVE CONTROLS, INC., Columbia, MO (US)

(*) Notice: Subject to any disclaimer, the term of this patent is extended or adjusted under 35 U.S.C. 154(b) by 0 days.

(21) Appl. No.: 15/759,051

(22) PCT Filed: Sep. 16, 2016

(86) PCT No.: PCT/US2016/052216
§ 371 (c)(1),
(2) Date: Mar. 9, 2018

(87) PCT Pub. No.: WO2017/049140
PCT Pub. Date: Mar. 23, 2017

(65) Prior Publication Data
US 2019/0241616 A1 Aug. 8, 2019

Related U.S. Application Data

(60) Provisional application No. 62/220,711, filed on Sep. 18, 2015.

(51) Int. Cl.
| | | |
|---|---|---|
| *A61K 38/00* | (2006.01) | |
| *A61K 38/08* | (2019.01) | |
| *A61K 45/06* | (2006.01) | |
| *C07K 7/06* | (2006.01) | |
| *C07K 7/14* | (2006.01) | |
| *A61P 35/00* | (2006.01) | |

(52) U.S. Cl.
CPC .............. *C07K 7/14* (2013.01); *A61K 38/085* (2013.01); *A61K 45/06* (2013.01); *A61P 35/00* (2018.01); *C07K 7/06* (2013.01); *A61K 38/00* (2013.01)

(58) Field of Classification Search
CPC ...... A61K 38/00; A61K 38/08; A61K 38/085; A61K 45/06; A61P 35/00; C07K 7/06; C07K 7/14
USPC .......... 514/1.1, 13.3, 21.6, 19.2, 19.3, 19.4, 514/19.5, 19.6; 530/300, 327
See application file for complete search history.

(56) References Cited

U.S. PATENT DOCUMENTS

| | | | | |
|---|---|---|---|---|
| 4,966,848 A | * | 10/1990 | Smith | ................. C12N 9/1029 435/193 |
| 5,223,421 A | * | 6/1993 | Smith | ................. C12N 9/1029 435/193 |
| 5,837,218 A | * | 11/1998 | Peers | .................. A61K 51/088 424/1.69 |
| 6,239,109 B1 | | 5/2001 | Rodgers et al. | |
| 6,455,500 B1 | | 9/2002 | Rodgers et al. | |
| 7,375,073 B2 | | 5/2008 | Tallant et al. | |
| 8,034,781 B2 | | 10/2011 | Tallant et al. | |
| 8,084,489 B2 | | 12/2011 | Chappell et al. | |
| 8,541,545 B2 | | 9/2013 | Gruber | |
| 9,233,978 B2 | | 1/2016 | Guo et al. | |
| 9,534,018 B2 | | 1/2017 | Gruber | |
| 2004/0176302 A1 | | 9/2004 | Rodgers et al. | |
| 2008/0167251 A1 | | 7/2008 | Tallant et al. | |
| 2010/0121027 A1 | | 5/2010 | Sharma et al. | |
| 2010/0137417 A1 | | 6/2010 | Chappell et al. | |
| 2013/0183367 A1 | | 7/2013 | Souza dos Santos et al. | |
| 2014/0005358 A1 | | 1/2014 | Lee et al. | |
| 2014/0296143 A1 | | 10/2014 | Tallant et al. | |
| 2015/0246093 A1 | | 9/2015 | Franklin et al. | |
| 2015/0252057 A1 | | 9/2015 | Guo et al. | |
| 2017/0081383 A1 | | 3/2017 | Gruber | |
| 2017/0247414 A1 | | 8/2017 | Gruber | |

FOREIGN PATENT DOCUMENTS

| | | |
|---|---|---|
| WO | 2009/061411 A2 | 5/2009 |
| WO | 2014190152 | 11/2014 |
| WO | 2016138288 | 9/2016 |

OTHER PUBLICATIONS

Berge, Stephen M. et al., "Pharmaceutical Salts," J. Pharm. Sci., vol. 66, No. 1, pp. 1-19, Jan. 1977.
Cook, Katherine L. et al., "Angiotensin-(1-7) Reduces Fibrosis in Orthotopic Breast Tumors," Cancer Research, vol. 70, No. 21, pp. 8319-8328, Nov. 1, 2010.
Der Torossian, Torres Marcelo et al., "Highly Potential Antiplasmodial Restricted Peptides", Chem Biol Drug Des, vol. 85, pp. 163-171, 2015.
Gallaher, P. E. et al., "Angiotensin-(1-7): A Peptide Hormone with Anti-Cancer Activity", Current Medicinal Chemistry, vol. 21, No. 1, pp. ???-???, 2014.
Isidro-Llobet, Albert et al., "Amino Acid-Protecting Groups", Chemical Reviews, vol. 109, pp. 2455-2504, 2009.
Krishnan, Bhavani et al., "Angiotensin-(1-7) Reduces Proliferation and Angiogenesis of Human Prostate Cancer Xenografts With a Decrease in Angiogenic Factors and an Increase in sFlt-1," The Prostate, vol. 73, No. 1, pp. 60-70, 2013.

(Continued)

*Primary Examiner* — Julie Ha
(74) *Attorney, Agent, or Firm* — Kilpatrick Townsend & Stockton LLP

(57) ABSTRACT

Angiotensin (1-7) analogs are provided. Also provided are methods of making such analogs methods for using analogs as therapeutic compositions such as, for example, treatment cancer.

30 Claims, 11 Drawing Sheets

Specification includes a Sequence Listing.

(56) References Cited

OTHER PUBLICATIONS

PCT/US2016/052216, "International Preliminary Report on Patentability", dated Mar. 29, 2018.
PCT/US2016/052216, "International Search Report and Written Opinion", dated Mar. 24, 2017.
PCT/US2016/052216, "Invitation to pay Additional Fees", dated Dec. 1, 2016.
Petty, W. Jeffrey et al., "Phase I and Pharmacokinetic Study of Angiotensin-(1-7), an Endogenous Antiangiogenic Hormone", Clinical Cancer Research, vol. 15, No. 23, pp. 7398-7404, Dec. 1, 2009.
Petty, W. Jeffrey et al., "Reverse translation of phase 1 biomarker findings links the activity of angiotensin-(-1-7) to repression of hypoxia inducible factor-1a in vascular sarcomas," BMC Cancer 2012, vol. 12, No. 404, pp. ???-???, 2012.
Rodgers, Kathleen E. et al., "Phase I/II dose escalation study of angiotensin 1-7 [A(1-7)] administered before and after chemotherapy in patients with newly diagnosed breast cancer," Cancer Chemother Pharmacol, vol. 57, pp. 559-568, 2006.
Soto-Pantoja, David R. et al., "Angiotensin-(-7) inhibits angiogenesis in human lung cancer xenografts with a reduction in vascular endothelial growth factor", Molecular Cancer Therapeutics, vol. 8, No. 6, pp. 1676-1683, Jun. 9, 2009.
Van Elden, L. J. R., et al., "Applicability of a Real-Time Quantitative PCR Assay for Diagnosis of Respiratory Syncytial Virus Infection in Immunocompromised Adults", Journal of Clinical Microbiology, pp. 4378-4381, Sep. 2003.
PCT/US2016/066181, "International Preliminary Report on Patentability", dated Jun. 21, 2018, 6 pages.
PCT/US2016/066181, "International Search Report and Written Opinion", dated Mar. 13, 2017, 8 pages.
EP 16847429.4, "Extended European Search Report", dated Feb. 25, 2019, 8 pages.
EP16874055.3, "Extended European Search Report", dated Jul. 16, 2019, 8 pages.
"Addendum to Abstracts presented at the 14th International Congress on Amino Acids, Peptides and Proteins, Amino Acids", Amino Acids, vol. 48, Issue 2, published online Jan. 29, 2016, presentation abstracts published at conference on Aug. 3, 2015 (no presentation made at conference), pp. 615-636.
"14th International Congress on Amino Acids, Peptides and Proteins", Conference Program, Vienna, Austria, Aug. 3-7, 2015, 2 pages.
Acuna et al., "Restoration of Muscle Strength in Dystrophic Muscle by Angiotensin-1-7 through Inhibition of TGF-β Signalling", Human Molecular Genetics, vol. 23, No. 5, Mar. 1, 2014, pp. 1237-1249.
Andrade et al., "Proteomic White Adipose Tissue Analysis of Obese Mice Fed with a High-Fat Diet and Treated with Oral Angiotensin-(1-7)", Peptides, vol. 60, 2014, pp. 56-62.
Benter , "Angiotensin-(1-7) Prevents Diabetes-Induced Cardiovascular Dysfunction", Am J. Physiol. Heart Circ. Physiol., vol. 292, No. 1, Jan. 2007, pp. H666-H672.
Brosnihan , "Angiotensin-(1-7) Dilates Canine Coronary Arteries Through Kinins and Nitric Oxide", Hypertension, vol. 27, No. 3, Mar. 1996, pp. 523-528.
Chappell , "Update on the Angiotensin Converting Enzyme 2-Angiotensin (1-7)-Mas Receptor Axis: Fetal Programing, Sex Differences, and Intracellular Pathways", Frontiers in Endocrinology, vol. 4, No. 201, Jan. 9, 2014, pp. 1-13.
Chipens et al., "Fragments of Immunoglobulins, Anaphylotoxins, and Kinins as Model Compounds for Studying Allergic Reactions", Proceedings of the Sixth USSR-FRG Symposium on Chemistry of Peptides and Proteins, vol. 4, Issue No. 1, Jan. 1, 1989, pp. 285-290.
Da Costa Goncalves et al., "Evidence that the Vasodilator Angiotensin-(1-7)-Mas Axis Plays an Important Role in Erectile Function", AJP Heart and Circulatory Physiology, vol. 293, No. 4, Nov. 2007 , pp. H2588-H2596.
Da Silverla et al., "Anti-Inflammatory Effects of the Activation of the Angiotensin-(1-7) Receptor, Mas, in Experimental Models of Arthritis", The Journal of Immunology, vol. 185, No. 9, Nov. 1, 2010, pp. 5569-5576.
De Vries et al., "Oral and Pulmonary Delivery of Thioether-Bridged Angiotensin-(1-7)", Peptides, vol. 31, Issue No. 5, May 1, 2010, pp. 893-898.
El-Hashim et al., "Angiotensin-(1-7) Inhibits Allergic Inflammation, via the Mas1 Receptor, Through Suppression of Erk1/2- and Nf-κB-Dependent Pathways", British Journal of Pharmacol, vol. 166, Jul. 2012, pp. 1964-1976.
O'Reilly et al., "Synthesis of a Conformationally Constrained δ-amino Acid Building Block", Amino Acids, vol. 44, Aug. 1, 2012, pp. 511-518.
Wester et al., "Biological Screening of Angiotensin-(1-7) Analogues Incorporating the Non-natural Delta-Amino Acid ACCA", Amino Acids, 14th International Congress on Amino Acids, Peptides and Proteins, vol. 48, No. 2, Aug. 2015, p. 636.
Wester, A. et al., "Synthesis of the Non-natural δ-Amino Acid ACCA and its Incorporation into Peptidomimetics by Solid Phase Peptide Synthesis," Excerpts—Abstract P20, published in Recent Advances in Synthesis & Chemical Biology XIII Symposium Program, Dublin, Ireland, Dec. 12, 2014, 11 pages.
Wester, A. et al., "Synthesis of the Non-natural δ-Amino Acid ACCA and its Incorporation into Peptidomimetics by Solid Phase Peptide Synthesis," Poster, presented at Recent Advances in Synthesis & Chemical Biology XIII Symposium, Dublin, Ireland, Dec. 12, 2014, 1 page.

* cited by examiner

SEQUENCE LISTING

```
<160> NUMBER OF SEQ ID NOS: 31

<210> SEQ ID NO 1
<211> LENGTH: 7
<212> TYPE: PRT
<213> ORGANISM: Artificial Sequence
<220> FEATURE:
<223> OTHER INFORMATION: synthetic peptide Ang-(1-7)

<400> SEQUENCE: 1

Asp Arg Val Tyr Ile His Pro
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic cyclic peptide TCAng01
<220> FEATURE:
<221> NAME/KEY: MISC_FEATURE
<222> LOCATION: (1)..(8)
<223> OTHER INFORMATION: cyclic peptide with position 1 Asp and position
      8 Asp joined

<400> SEQUENCE: 2

Asp Arg Val Tyr Ile His Pro Asp
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic cyclic peptide TCAng02
<220> FEATURE:
<221> NAME/KEY: MOD_RES
<222> LOCATION: (1)..(1)
<223> OTHER INFORMATION: Xaa is Asp; Asp is modified by acetylation
<220> FEATURE:
<221> NAME/KEY: MISC_FEATURE
<222> LOCATION: (2)..(8)
<223> OTHER INFORMATION: cyclic peptide with position 2 Arg and position
      8 Asp joined

<400> SEQUENCE: 3

Xaa Arg Val Tyr Ile His Pro Asp
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic cyclic peptide TCAng03
```

```
<220> FEATURE:
<221> NAME/KEY: MISC_FEATURE
<222> LOCATION: (1)..(8)
<223> OTHER INFORMATION: cyclic peptide with position 1 Asp and position
      8 Asp joined

<400> SEQUENCE: 4

Asp Arg Val Tyr Ile His Pro Asp
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic cyclic peptide TCAng04
<220> FEATURE:
<221> NAME/KEY: MISC_FEATURE
<222> LOCATION: (1)..(8)
<223> OTHER INFORMATION: cyclic peptide with position 1 Asp and position
      8 Asp joined
<220> FEATURE:
<221> NAME/KEY: MOD_RES
<222> LOCATION: (8)..(8)
<223> OTHER INFORMATION: Asp modified by two amino acid extension
      D-valine-D-proline (dV-dP), with amidation of dP

<400> SEQUENCE: 5

Asp Arg Val Tyr Ile His Pro Asp
1               5

<210> SEQ ID NO 6
<211> LENGTH: 8
<212> TYPE: PRT
<213> ORGANISM: Artificial Sequence
<220> FEATURE:
<223> OTHER INFORMATION: synethtic cyclic peptide TCAng05
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by amino acid extension  D-valine-
      D-proline (dV-dP), with amination of dP

<400> SEQUENCE: 6

Asp Arg Val Tyr Ile His Pro Lys
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic peptide L-TCAng05
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
```

```
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 7

Asp Arg Val Tyr Ile His Pro Lys
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic cyclic peptide NEP1
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 8

Asp Arg Val Tyr Ile Ala Pro Lys
1               5

<210> SEQ ID NO 9
<211> LENGTH: 8
<212> TYPE: PRT
<213> ORGANISM: Artificial Sequence
<220> FEATURE:
<223> OTHER INFORMATION: synthetic cyclic peptide NEP2
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(8)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by amino acid extension D-valine
      (dV), with amidation of dV

<400> SEQUENCE: 9

Asp Arg Val Tyr Ile His Pro Lys
1               5
```

```
<210> SEQ ID NO 10
<211> LENGTH: 8
<212> TYPE: PRT
<213> ORGANISM: Artificial Sequence
<220> FEATURE:
<223> OTHER INFORMATION: synthetic cyclic peptide NEP3
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(8)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 10

Asp Arg Val Ala Ile His Pro Lys
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic cyclic peptide NEP4
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 11

Asp Arg Val Tyr Ala His Pro Lys
1               5

<210> SEQ ID NO 12
<211> LENGTH: 8
<212> TYPE: PRT
<213> ORGANISM: Artificial Sequence
<220> FEATURE:
<223> OTHER INFORMATION: synthetic cyclic peptide NEP5
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
```

```
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 12

Asp Arg Val Tyr Ile His Ala Lys
1               5

<210> SEQ ID NO 13
<211> LENGTH: 8
<212> TYPE: PRT
<213> ORGANISM: Artificial Sequence
<220> FEATURE:
<223> OTHER INFORMATION: synthetic cyclic peptide NEP6
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) Leu
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 13

Asp Arg Val Tyr Ile His Pro Lys
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic cyclic peptide NEP7
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
```

```
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 14

Asp Arg Ala Tyr Ile His Pro Lys
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic cyclic peptide NEP8
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: amidated Lys

<400> SEQUENCE: 15

Asp Arg Val Tyr Ile His Pro Lys
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic cyclic peptide NEP9
<220> FEATURE:
<221> NAME/KEY: MISC_FEATURE
<222> LOCATION: (1)..(8)
<223> OTHER INFORMATION: cyclic peptide with position 1 Ala and position
      8 Lys joined
<220> FEATURE:
<221> NAME/KEY: MOD_RES
<222> LOCATION: (1)..(1)
<223> OTHER INFORMATION: Ala modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 16

Ala Arg Val Tyr Ile His Pro Lys
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic cyclic peptide NEP10
```

```
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) Ala
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 17

Asp Arg Val Tyr Ile His Pro Lys
1               5

<210> SEQ ID NO 18
<211> LENGTH: 8
<212> TYPE: PRT
<213> ORGANISM: Artificial Sequence
<220> FEATURE:
<223> OTHER INFORMATION: synthetic cyclic peptide NEP11
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 18

Asp Arg Val Phe Ile His Pro Lys
1               5

<210> SEQ ID NO 19
<211> LENGTH: 8
<212> TYPE: PRT
<213> ORGANISM: Artificial Sequence
<220> FEATURE:
<223> OTHER INFORMATION: synthetic cyclic peptide NEP12
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
```

```
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 19

Asp Arg Val Tyr Leu His Pro Lys
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic cyclic peptide NEP13
<220> FEATURE:
<221> NAME/KEY: MISC_FEATURE
<222> LOCATION: (1)..(8)
<223> OTHER INFORMATION: cyclic peptide with position 1 Asp and position
      8 2,3-diaminopropionic acid (Dap) joined
<220> FEATURE:
<221> NAME/KEY: MISC_FEATURE
<222> LOCATION: (1)..(8)
<223> OTHER INFORMATION: lactam bridge between position 1 Asp and
      position 8 2,3-diaminopropionic acid (Dap)
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MOD_RES
<222> LOCATION: (8)..(8)
<223> OTHER INFORMATION: 2,3-diaminopropionic acid (Dap) modified by two
      amino acid extension D-valine-D-proline (dV-dP), with amidation of
      dP

<400> SEQUENCE: 20

Asp Arg Val Tyr Ile His Pro Xaa
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic cyclic peptide NEP14
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) norvaline (Nva)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP
```

```
<400> SEQUENCE: 21

Asp Arg Val Tyr Ile His Pro Lys
1               5

<210> SEQ ID NO 22
<211> LENGTH: 8
<212> TYPE: PRT
<213> ORGANISM: Artificial Sequence
<220> FEATURE:
<223> OTHER INFORMATION: synthetic cyclic peptide NEP15
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (1)..(1)
<223> OTHER INFORMATION: Asp modified by amino acid extension with
      aceylated (Ac) azidohomoalanine (Aha)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 22

Asp Arg Val Tyr Ile His Pro Lys
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic cyclic peptide NEP16
<220> FEATURE:
<221> NAME/KEY: MOD_RES
<222> LOCATION: (1)..(1)
<223> OTHER INFORMATION: Asp modified by amino acid extension with
      aminated (NH2) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 23

Asp Arg Val Tyr Ile His Pro Lys
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic cyclic peptide NEP17
```

```
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (4)..(4)
<223> OTHER INFORMATION: Xaa is N-methyl tyrosine (NMeY)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 24

Asp Arg Val Xaa Ile His Pro Lys
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic cyclic peptide NEP18
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (6)..(6)
<223> OTHER INFORMATION: Xaa is N-methyl histidine (NMeH)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 25

Asp Arg Val Tyr Ile Xaa Pro Lys
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic cyclic peptide NEP19
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
```

-continued

```
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (5)..(5)
<223> OTHER INFORMATION: Xaa is N-methyl isoleucine (NMeI)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 26

Asp Arg Val Tyr Xaa His Pro Lys
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic cyclic peptide NEP20
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 N-methyl lysine (NMeK) joined
<220> FEATURE:
<221> NAME/KEY: MISC_FEATURE
<222> LOCATION: (1)..(8)
<223> OTHER INFORMATION: lactam bridge between Asp at position 1 and
      N-methyl lysine (NMeK) at position 8
<220> FEATURE:
<221> NAME/KEY: MOD_RES
<222> LOCATION: (8)..(8)
<223> OTHER INFORMATION: N-methyl lysine (NMeK) modified by two amino
      acid extension D-valine-D-proline (dV-dP), with amidation of dP
<220> FEATURE:
<221> NAME/KEY: MOD_RES
<222> LOCATION: (8)..(8)
<223> OTHER INFORMATION: Xaa is N-methyl lysine (NMeK)

<400> SEQUENCE: 27

Asp Arg Val Tyr Ile His Pro Xaa
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic cyclic peptide NEP21
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
```

```
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (3)..(3)
<223> OTHER INFORMATION: Xaa is N-methyl valine (NMeV)
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 28

Asp Arg Xaa Tyr Ile His Pro Lys
1               5

<210> SEQ ID NO 29
<211> LENGTH: 8
<212> TYPE: PRT
<213> ORGANISM: Artificial Sequence
<220> FEATURE:
<223> OTHER INFORMATION: synthetic cyclic peptide NEP22
<220> FEATURE:
<221> NAME/KEY: MOD_RES
<222> LOCATION: (1)..(1)
<223> OTHER INFORMATION: Asp modified by amino acid extension with
      aceylated (Ac) 2-Aminobutyric acid (Abu)
<220> FEATURE:
<221> NAME/KEY: MISC_FEATURE
<222> LOCATION: (1)..(8)
<223> OTHER INFORMATION: cyclic peptide with position 1 Asp and position
      8 Lys joined
<220> FEATURE:
<221> NAME/KEY: MISC_FEATURE
<222> LOCATION: (1)..(8)
<223> OTHER INFORMATION: lactam bridge between Asp at position 1 and Lys
      at position 8
<220> FEATURE:
<221> NAME/KEY: MOD_RES
<222> LOCATION: (8)..(8)
<223> OTHER INFORMATION: Lys modified by two amino acid extension
      D-valine-D-proline (dV-dP), with amidation of dP

<400> SEQUENCE: 29

Asp Arg Val Tyr Ile His Pro Lys
1               5

<210> SEQ ID NO 30
<211> LENGTH: 8
<212> TYPE: PRT
<213> ORGANISM: Artificial Sequence
<220> FEATURE:
<223> OTHER INFORMATION: synthetic cyclic peptide NEP23
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 ornithine (Orn) joined
<220> FEATURE:
<221> NAME/KEY: MISC_FEATURE
<222> LOCATION: (1)..(8)
<223> OTHER INFORMATION: lactam bridge between Asp at position 1 and
      ornithine (Orn) at position 8
```

```
<220> FEATURE:
<221> NAME/KEY: MOD_RES
<222> LOCATION: (8)..(8)
<223> OTHER INFORMATION: ornithine (Orn) modified by two amino acid
      extension D-valine-D-proline (dV-dP), with amidation of dP
<220> FEATURE:
<221> NAME/KEY: MOD_RES
<222> LOCATION: (8)..(8)
<223> OTHER INFORMATION: Xaa is ornithine (Orn)

<400> SEQUENCE: 30

Asp Arg Val Tyr Ile His Pro Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: synthetic cyclic peptide NEP24
<220> FEATURE:
<221> NAME/KEY: MOD_RES
<222> LOCATION: (1)..(1)
<223> OTHER INFORMATION: Asp modified by amino acid extension with
      aceylated (Ac) norleucine (Nle)
<220> FEATURE:
<221> NAME/KEY: MISC_FEATURE
<222> LOCATION: (1)..(8)
<223> OTHER INFORMATION: cyclic peptide with position 1 Asp and position
      8 2,4-diaminobutyric acid (Dab) joined
<220> FEATURE:
<221> NAME/KEY: MISC_FEATURE
<222> LOCATION: (1)..(8)
<223> OTHER INFORMATION: lactam bridge between Asp at position 1 and L2,
      4-diaminobutyric acid (Dab)ys at position 8
<220> FEATURE:
<221> NAME/KEY: MOD_RES
<222> LOCATION: (8)..(8)
<223> OTHER INFORMATION: 2,4-diaminobutyric acid (Dab) modified by two
      amino acid extension D-valine-D-proline (dV-dP), with amidation of
      dP
<220> FEATURE:
<221> NAME/KEY: MOD_RES
<222> LOCATION: (8)..(8)
<223> OTHER INFORMATION: Xaa is 2,4-diaminobutyric acid (Dab)

<400> SEQUENCE: 31

Asp Arg Val Tyr Ile His Pro Xaa
1               5
```

ANGIOTENSIN (1-7) ANALOGS AND METHODS RELATING THERETO

CROSS-REFERENCE TO RELATED APPLICATIONS

This application is a U.S. national phase of International Application No. PCT/US2016/052216, filed on Sep. 16, 2016 and published as International Publication No. WO 2017/049140 A2 on Mar. 23, 2017, which application claims the benefit of and priority to U.S. Provisional Patent Application Ser. No. 62/220,711, filed Sep. 18, 2015, the contents of all of which are herein incorporated by reference in their entireties.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 1078945_SEQLISTING, created on Dec. 12, 2018, and having a size of 20.5 KB. The sequence listing contained in this ASCII formatted document is part of the specification and is herein incorporated by reference in its entirety.

BACKGROUND

Angiotensin-(1-7) ("Ang(1-7)") inhibits the growth of human lung, breast and prostate cancer cells and tumors, through effects on proliferation, inflammation, angiogenesis, fibrosis and metastasis. In addition, the heptapeptide hormone has a good safety profile and shows efficacy in patients with cancer. As a seven amino acid peptide, the half-life of Ang-(1-7) in vivo is short; in human studies, the half-life in patients administered the heptapeptide hormone for the treatment of cancer was between 25 and 37 min (Petty et al., Clinical Cancer Research 2009; 15:7398-404) in agreement with previous studies in breast cancer patients treated with Ang-(1-7) as adjuvant therapy (Rodgers et al., Cancer Chemother. Pharmacol. 2006; 57:559-68).

BRIEF SUMMARY

Described herein are angiotensin (1-7) peptide analogs for use as agonists for the angiotensin (1-7) receptor mas. Also provided herein are methods for use of the peptide analogs in treating cancer in a subject. A class of angiotensin (1-7) peptide analogs described herein includes peptides of the following formula $R^1$—Z—$R^9$—$Y^1$ and pharmaceutically acceptable salts thereof. In these peptides, $R_1$ is norleucine (Nle), leucine (L), alanine (A), norvaline (Nva), azidohomoalanine (Aha), or 2-Aminobutyric acid (Abu); Z is an amino acid sequence having at least 85% identity to SEQ ID NO:1, wherein in Z has the formula $R^2$—$R^3$—$R^4$—$R^5$—$R^6$—$R^7$—$R^8$; $R^9$ is lysine (K), ornithine (Orn), 2,3-diaminopropionic acid (Dap), 2,4-diaminobutyric acid (Dab), or N-methyl lysine (NMe-K); and $Y^1$ is absent or is a single amino acid extension or a two amino acid extension attached to $R^9$. In addition, $R^1$—Z—$R^9$ has a cyclic structure, wherein $R^1$ or $R^2$ is connected to $R^9$.

Also described herein are pharmaceutical compositions including a compound as described herein and a pharmaceutically acceptable carrier.

Further described herein are methods of treating or preventing cancer in a subject. The methods of treating or preventing cancer in a subject comprise administering to the subject an effective amount of an angiotensin (1-7) peptide analog, or pharmaceutical composition comprising such an analog, as described herein. Optionally, the cancer may be a cancer that expresses, or over-expresses, the angiotensin (1-7) receptor mas. A pharmaceutically effective amount may be an amount that is sufficient to inhibit cell growth or proliferation, angiogenesis, or fibrosis.

The method can further comprise administering a second therapeutic agent to the subject. The second therapeutic agent can be a chemotherapeutic agent.

Also described herein are methods of inhibiting the angiotensin (1-7) receptor mas in a cell. The methods comprise contacting the cell with an effective amount of the peptide as described herein. The cell expresses the angiotensin (1-7) receptor mas. The contacting can be performed in vivo or in vitro.

The details of one or more aspects and embodiments are set forth in the description and drawings below. Other features, objects, and advantages will be apparent from the description and drawings, and from the claims.

DETAILED DESCRIPTION

Described herein are angiotensin (1-7) peptide analogs and methods for their use. The angiotensin (1-7) peptide analogs described herein effectively inhibit growth of various cancer cells in vitro and in vivo.

I. Angiotensin (1-7) Analogs

A class of Ang(1-7) peptide analogs described herein is represented generally by Formula I: $R^1$—Z—$R^9$—$Y^1$ and pharmaceutically acceptable salts thereof. $R^1$—Z—$R^9$ has a cyclic structure, wherein $R^1$ or $R^2$ is connected to $R^9$.

In Formula I, $R^1$ may be norleucine (Nle), leucine (L), alanine (A), norvaline (Nva), azidohomoalanine (Aha), or 2-Aminobutyric acid (Abu). In some instance, $R^1$ may be modified with a —COCH₃ group (acetylated) or modified with a —NH₂ group (aminated).

Also in Formula I, Z is an amino acid sequence having at least 85% identity to SEQ ID NO:1, wherein in Z has the formula $R^2$—$R^3$—$R^4$—$R^5$—$R^6$—$R^7$—$R^8$. SEQ ID NO:1 is the native sequence of the angiotensin (1-) peptide. In some instances, Z may include at least one conservative amino acid substitution. In certain instances, Z may include at least one a non-conservative amino acid substitution. In some instances, Z may include natural amino acids, non-natural amino acids, or both natural and non-natural amino acids. In some instances, Z may include L form amino acids. In some instances, Z may include D form amino acids. In some instances, Z may include both L form and D form amino acids. In some instances, Z may contain one or more methylated amino acids. For example, Z may include at least one amino acid substitution in which substitution is with alanine, phenylalanine, leucine, N-methyl tyrosine, N-methyl histidine, N-methyl isoleucine, or N-methyl valine. In some instances, $R^2$ may be aspartic acid or alanine. In some cases, $R^4$ may be valine, alanine, or N-methyl valine. In certain instances, $R^5$ may be tyrosine, N-methyl tyrosine, phenylalanine, or alanine. In some instances, $R^6$ may be isoleucine, N-methyl isoleucine, alanine, or leucine. In some cases, $R^7$ may be histidine, N-methyl histidine, or alanine. In certain instances, $R^8$ may be proline or alanine.

Also in Formula I, $R^9$ may be lysine (K), ornithine (Orn), 2,3-diaminopropionic acid (Dap), 2,4-diaminobutyric acid (Dab), or N-methyl lysine (NMe-K). Optionally, $R^9$ may be modified by —$NH_2$ (amidated).

In Formula I, $Y^1$ may be absent or may be a single amino acid extension or a two amino acid extension attached to $R^9$. For example, $Y^1$ may be D-valine-D-proline (dV-dP), D-valine (dV), or D-proline (dP), or may be absent. In some instances, $R^9$ may be modified with an —$NH_2$ if $Y_1$ is absent. For example, the peptide may have a lactam bridge between the amino acid at position $R^1$ or $R^2$ and the amino acid at position $R^9$. In some instances, the lactam bridge is between the amino acid at $R^2$ and the amino acid at position $R^9$, referred to herein as "[Lac2,9]".

Figure 1A:
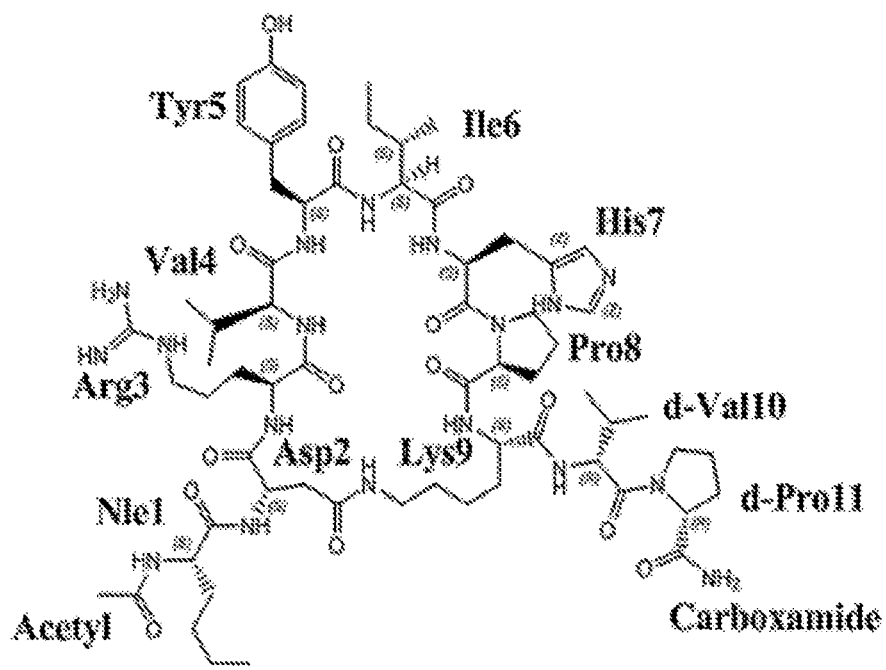
FIG. 1A shows an exemplary Ang(1-7) peptide analog designated as TCAng05 (SEQ ID NO:6) according to one aspect. The chemical formula of peptide is $C_6H_{102}N_{18}O_{14}$, and the molecular weight is 1359.64 Da.

An example of Formula I is shown in FIG. 1A. The peptide shown in FIG. 1A has the sequence [Lac(2,9)]Ac-(Nle)cyc[DRVYIHPK](dV)(dP)-amide, as set forth in SEQ ID NO:6.

Additional examples of Ang(1-7) peptide analogs include the peptides identified in Table 1 and as set forth in SEQ ID NOs:2-31. In some instances, the peptide has an amino acid sequence selected from SEQ ID NOs: 5, 6, 8-31. In certain cases, the peptide has an amino acid sequence of any one of SEQ ID NOs: 5, 6, 11, 15, 23, 27, or 31. In one example, the peptide has the amino acid sequence set forth in SEQ ID NO:6.

TABLE 1

Ang(1-7) Peptide and Analogs

| Peptide Name | Peptide Sequence | SEQ ID NO |
|---|---|---|
| Ang-(1-7) | DRVYIHP | SEQ ID NO: 1 |
| TCAng01 | cyc[DRVYIHPD] | SEQ ID NO: 2 |
| TCAng02 | Ac-(D)cyc[RVYIHPD] | SEQ ID NO: 3 |
| TCAng03 | cyc[DRVYIHPD] | SEQ ID NO: 4 |
| TCAng04 | cyc[DRVYIHPD](dV)(dP)-amide | SEQ ID NO: 5 |
| TCAng05 | [Lac(2,9)]Ac-(Nle)cyc[DRVYIHPK](dV)(dP)-amide | SEQ ID NO: 6 |
| L-TCAng05 | Ac-(Nle)DRVYIHPK(dP)-amide | SEQ ID NO: 7 |
| NEP1 | [Lac(2,9)]Ac-(Nle)cyc[DRVYIAPK](dV)(dP)-amide | SEQ ID NO: 8 |
| NEP2 | [Lac(2,9)]Ac-(Nle)cyc[DRVYIHPK](dV)-amide | SEQ ID NO: 9 |
| NEP3 | [Lac(2,9)]Ac-(Nle)cyc[DRVAIHPK](dV)(dP)-amide | SEQ ID NO: 10 |
| NEP4 | [Lac(2,9)]Ac-(Nle)cyc[DRVYAHPK](dV)(dP)-amide | SEQ ID NO: 11 |
| NEP5 | [Lac(2,9)]Ac-(Nle)cyc[DRVYIHAK](dV)(dP)-amide | SEQ ID NO: 12 |
| NEP6 | [Lac(2,9)]Ac-(L)cyc[DRVYIHPK](dV)(dP)-amide | SEQ ID NO: 13 |
| NEP7 | [Lac(2,9)]Ac-(Nle)cyc[DRAYIHPK](dV)(dP)-amide | SEQ ID NO: 14 |
| NEP8 | [Lac(2,9)]Ac-(Nle)cyc[DRVYIHP(K)-amide] | SEQ ID NO: 15 |
| NEP9 | Ac-(Nle)cyc[ARVYIHPK](dV)(dP)-amide | SEQ ID NO: 16 |
| NEP10 | [Lac(2,9)]Ac-(A)cyc[DRVYIHPK](dV)(dP)-amide | SEQ ID NO: 17 |
| NEP11 | [Lac(2,9)]Ac-(Nle)cyc[DRVFIHPK](dV)(dP)-amide | SEQ ID NO: 18 |
| NEP12 | [Lac(2,9)]Ac-(Nle)cyc[DRVY*L*HPK](dV)(dP)-amide | SEQ ID NO: 19 |
| NEP13 | [Lac(2,9)]Ac-(Nle)cyc[DRVYIHP(Dap)](dV)(dP)-amide | SEQ ID NO: 20 |
| NEP14 | [Lac(2,9)]Ac-(Nva)cyc[DRVYIHPK](dV)(dP)-amide | SEQ ID NO: 21 |
| NEP15 | [Lac(2,9)]Ac-(Aha)cyc[DRVYIHPK](dV)(dP)-amide | SEQ ID NO: 22 |
| NEP16 | [Lac(2,9)]H2N-(Nle)cyc[DRVYIHPK](dV)(dP)-amide | SEQ ID NO: 23 |
| NEP17 | [Lac(2,9)]Ac-(Nle)cyc[DRV(NMeY)IHPK](dV)(dP)-amide | SEQ ID NO: 24 |
| NEP18 | [Lac(2,9)]Ac-(Nle)cyc[DRVYI(NMeH)PK](dV)(dP)-amide | SEQ ID NO: 25 |

TABLE 1-continued

Ang(1-7) Peptide and Analogs

| Peptide Name | Peptide Sequence | SEQ ID NO |
|---|---|---|
| NEP19 | [Lac(2,9)]Ac-(Nle)cyc[DRVY(NMeI)HPK](dV)(dP)-amide | SEQ ID NO: 26 |
| NEP20 | [Lac(2,9)]Ac-(Nle)cyc[DRVYIHP(NMeK)](dV)(dP)-amide | SEQ ID NO: 27 |
| NEP21 | [Lac(2,9)]Ac-(Nle)cyc[DR(NMeV)YIHPK](dV)(dP)-amide | SEQ ID NO: 28 |
| NEP22 | [Lac(2,9)]Ac-(Abu)cyc[DRVYIHPK](dV)(dP)-amide | SEQ ID NO: 29 |
| NEP23 | [Lac(2,9)]Ac-(Nle)cyc[DRVYIHP(Orn)](dV)(dP)-amide | SEQ ID NO: 30 |
| NEP24 | [Lac(2,9)]Ac-(Nle)cyc[DRVYIHP(Dab)](dV)(dP)-amide | SEQ ID NO: 31 |

In one example, isoleucine at position $R^6$ is substituted with alanine, such as in NEP4 (SEQ ID NO:11). In another example, $Y^1$ is absent, such as in NEP8 (SEQ ID NO:15). In some instances, when $Y^1$ is absent, $R^9$ is modified, such as by amination. An example of this is NEP8 (SEQ ID NO:15). In some instances, $R^1$ may be amidated. For example, $R^1$ may be an amidated norleucine amino acid, such as in NEP 16 (SEQ ID NO:23). In some instances, $R^9$ may be a methylated amino acid. One example of this is NEP 20 (SEQ ID NO:27), which has a N-methylated lysine at position $R^9$. In some instances, the peptide may contain non-natural amino acids. For example, $Y^1$ may be a two amino acid extension attached to $R^9$. In one example, $R^9$ may be 2,4-diaminobutyric acid, such as in NEP24 (SEQ ID NO:31).

II. Methods of Making the Angiotensin (1-7) Analogs

The peptides described herein can be prepared in a variety of ways. The peptides can be synthesized using various synthetic methods. The peptides described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (such as $^1H$ or $^{13}C$) infrared spectroscopy, spectrophotometry (such as UV-visible), or mass spectrometry, or by chromatography such as high performance liquid chromatography (HPLC) or thin layer chromatography.

Peptides described by Formula I and pharmaceutically acceptable salts thereof can be made using the methods shown in Scheme 1.

Scheme 1:

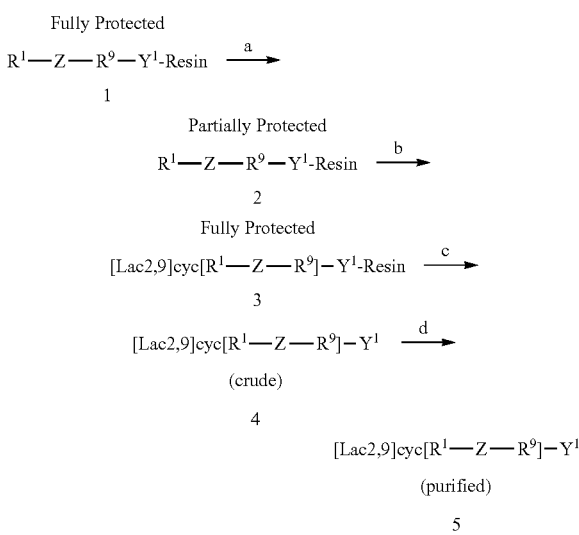

Reagents and conditions: (a) deprotecting agent; (b) coupling reagent; (c) deprotecting agent; (d) purification.

As depicted in Scheme 1, the compounds according to Formula I can be synthesized four steps following standard Fluorenylmethyloxycarbonyl (Fmoc) synthesis of the fully protected linear peptide (1). The peptide synthesis can be performed using $NH_2$-Sieber amide resin to which amino acid residues are sequentially added. The linear peptide is reacted with a deprotecting agent, such as trifluoroacetic acid (TFA), triisopropylsilane (TIPS), or both, remove protecting groups, yielding a partially protected (partially deprotect) linear peptide (2) in which the amino acid at either $R^1$ or the $R^2$ position of Z in Formula I and the amino acid at $R^9$ are deprotected. Optionally, the peptide may then be lyophilized. The deprotected linear peptide (2) treated with coupling reagents to form a fully protected cyclized peptide (3) via formation of a lactam bridge between the $R^1$ or $R^2$ position and the $R^9$ position of the peptide. Exemplary coupling agents are benzotriazol-1-yl-oxytripyrrolidino-phosphonium hexafluorophosphate (PyBOP) and Di-isopropylethylamine (DIEA). Optionally, following cyclization, the peptide may then be lyophized. The fully protected cyclized peptide (3) is treated with a deprotecting agent, such as TFA, to form crude deprotected cyclized peptide (4). A purification step, such as high performance liquid chromatography (HPLC), is taken to remove any impurities and yield the purified cyclic peptide of Formula I (5).

rophosphate (PyBOP) to yield cyclic peptide (3) bound to the resin. A final deprotection step using TFA removes the peptide from the resin to yield crude TCAng05 peptide (4). A purification step, such as HPLC, can be performed to yield purified TCAng05 peptide (5).

Scheme 2:

1 'fully protected' Ac-Nle-cyc(Asp(O-2-PhiPr)-RVYIHP-Lys(Mtt)-D-Val-D-Pro-NH-Resin

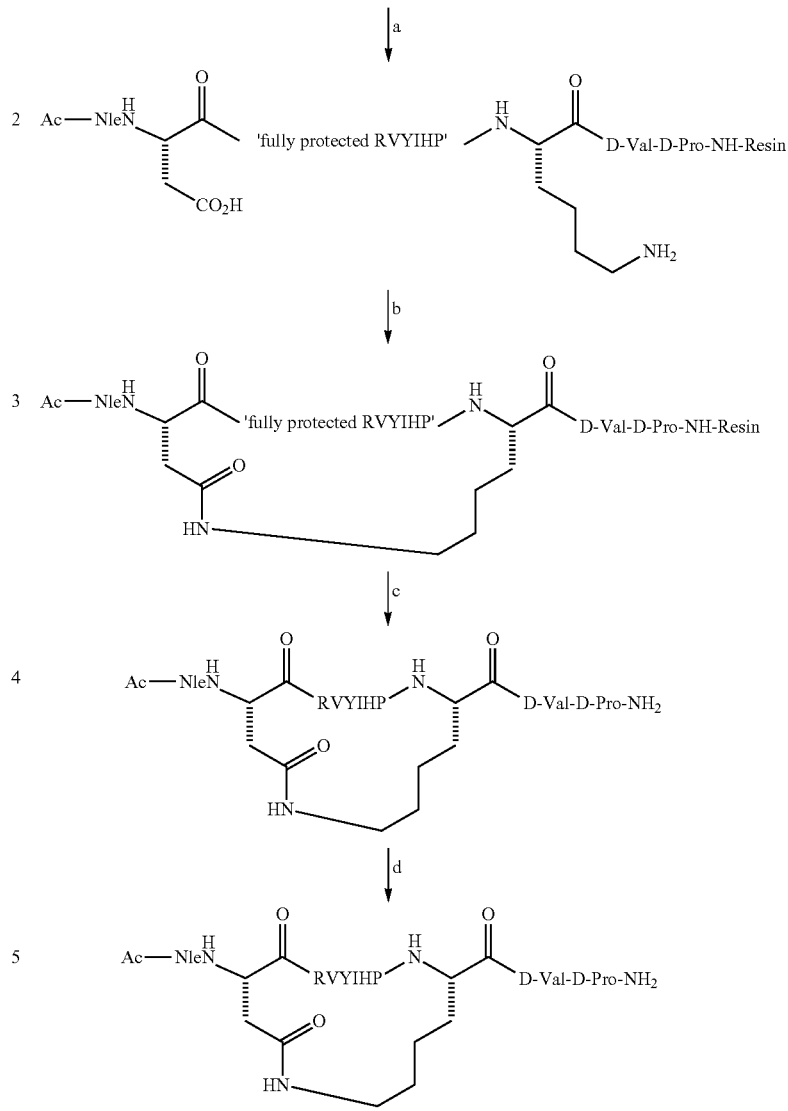

Reagents and conditions: (a) TFA; (b) lyophilization, DIEA + PyBOP; (c) lyophilization, TFA; (d) high performance liquid chromatography (HPLC).

One example peptide described by Formula I and pharmaceutically acceptable salts thereof can be made using the methods shown in Scheme 2, which depicts the synthesis of TCAng05 (SEQ ID NO:6) as depicted in FIG. 1A. As depicted in Scheme 2, the fully protected peptide (1) can be partially deprotected to remove protecting groups from the aspartic acid at $R^2$ (2-phenylisopropyloxy (O-2-PhiPr)) and the lysine at $R^9$ (4-methyltrityl (Mtt)) using TFA (e.g., 2.5%). The partially deprotected peptide (2) can be cyclized using coupling agents di-isopropylethylamine (DIEA) and benzotriazol-1-yl-oxytripyrrolidinophosphonium hexafluo- In some instances, the use of Sieber Amide Resin may allow for a C' terminal carboxamide to be synthesized and permits the release of the semi-protected peptide from the resin. This enables an in-solution cyclization to be carried out. All amino acids may be double coupled on an automated synthesis instrument (e.g., Pioneer) to help minimize truncations. Fmoc-K(mtt)-OH and Fmoc-Asp(O2-PhiPr)—OH may be used for their orthogonal protecting groups. Protecting groups may be removed at the same time as the peptide is cleaved from the resin, leaving the carboxyl and amine free for the cyclization step while leaving all other protecting groups in place. In some instances, the peptide may be completely assembled and acetylated on the synthesis instrument and cyclization. In some instances, the cleavage steps may be completed on the synthesis instrument or manually.

In some instances, the completed peptide resin may be prepared for protecting group cleavage by washing with any of dimethylformamide (DMF), methanol, and dichloromethane (DCM). For example, the resin may be washed sequentially with DMF, methanol, and DCM, three times each. After washing, the resin may dried overnight (e.g., using a lyophilizer). In some instances, cleavage may be carried out using one or more of TFA or triisopropysiane (TIPS). For example, cleavage may be carried out with a mixture of 2 ml TFA, 100 ul TIPS, and 100 ul of water, or a solution of 3% TFA/5% TIPS in DCM. In some instances, cleavage may be carried out at about 20° C.-26° C. In some instances, the cleavage removes the peptide from the resin as well as the protecting groups from protected amino acids (e.g., Lys and Asp). In some instances, following cleavage, the collected peptide may filtered and neutralized (e.g., using 10% pyridine in methanol to neutralize the TFA). The peptide may be then precipitated to a solid and, in some instances, washed and further lyophilized. HPLC may be carried out to observe target peptide as a major peak (e.g., 90%).

To cyclize the linear peptide, the peptide may be dissolved in a minimal amount of anhydrous DMF and then mixed with PyBOP and DIEA (e.g., at a ratio of 1:4:10). The mixture may be mixed for 10-20 hours (e.g., 12 hrs) at about 20° C.-26° C. In some instances, the reaction mixture may be mixed with acetonitrile (e.g., 7 volumes of a solution comprising 70% acetonitrile and 30% water) and then frozen. The frozen peptide may then be lyophilized, which removes a large amount of the DMF and facilitating cleavage of the peptide. Unwanted byproducts may be removed by HPLC.

In some instances, full cleavage of the peptide may be achieved using TFA and water, alone or in combination with Thioanisol and/or Ethyl Methyl Sulfide. An exemplary mixture is 80 ml of TFA, 4 ml of Water, 4 ml Thioanisol, 4 ml of Ethyl Methyl Sulfide and 4 ml of Ethanedithiol. The peptide may be shaken with the cleavage solution at about 20° C.-26° C. until cleavage is substantially achieved (e.g., 3 hours). Following cleavage, the peptide may be precipitated. An exemplary precipitation solution is −80° C. Ethyl Ether Anhydrous, used at several volumes of the peptide solution (e.g., 8× volume), but other solutions known in the art may also be used. Large peptide volumes may be split into smaller volumes to facilitate precipitation. Centrifugation can be used to pellet the precipitated peptide. Mixing the precipitated peptide with the precipitation solution may be performed multiple times. The precipitated peptide may be dried (e.g., air dried). In one example, the precipitated peptide may be mixed with 50/50 acetonitrile/water with 0.1% TFA, solubilized, frozen, and then lyophilized to dryness.

Figure 1B:
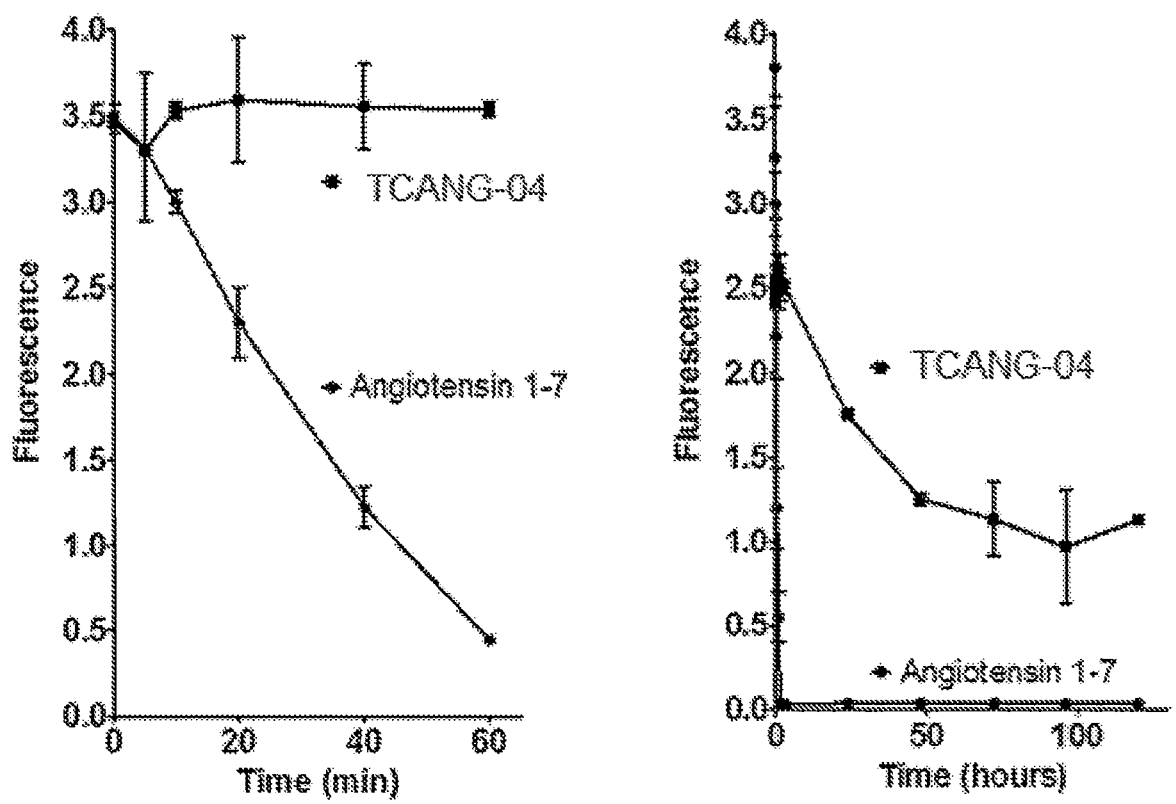
FIG. 1B shows graphs depicting the stability of TCAng04 (SEQ ID NO:5) in rat plasma incubated at 37° C.

In some instances, the peptide analogs described by Formula I and pharmaceutically acceptable salts thereof, or derivatives thereof, are more stable than native Ang(1-7) peptide. In some instances, the peptides have a longer half-life under physiological conditions than Ang(1-7) peptide. Physiological conditions are environments within the body of a subject to which the peptides may be administered. Exemplary physiological environments include blood, plasma, serum, saliva, and the environments of the gastrointestinal tract, the nasal passage, the respiratory tract, and the lungs. For example, Ang(1-7) has a half-life of 30 minutes in plasma. In some instances, the half-life of the peptides described herein, and pharmaceutically acceptable salts or derivatives thereof, may be at least about 2 times, 3 times, 4 times, 5 times, 6, times, 10 times, 15 times, 20 times, 40 times, 60 times, 80 times, 100 times, 125 times, 150 times, 175 times, or 200 times longer. In one example, TCAng04 may have a half life of 50 hours in rat plasma, as shown in FIG. 1B. Thus, in some instances, the peptides described and pharmaceutically acceptable salts or derivatives thereof, may be at least about 100× more stable in plasma than Ang(1-7).

III. Pharmaceutical Formulations

The peptides described herein or derivatives thereof can be provided in a pharmaceutical composition. Depending on the intended mode of administration, the pharmaceutical composition can be in the form of solid, semi-solid, liquid dosage forms, or combinations thereof, such as, for example, tablets, suppositories, pills, capsules, powders, liquids, or suspensions, preferably in unit dosage form suitable for single administration of a precise dosage. The compositions include a pharmaceutically effective amount of the peptides described herein, or derivatives thereof, in combination with a pharmaceutically acceptable carrier and, in addition, may include other medicinal agents, pharmaceutical agents, carriers, or diluents. The term pharmaceutically acceptable refers to a material that is not biologically or otherwise undesirable, which can be administered to an individual along with the selected compound without causing unacceptable biological effects or interacting in a deleterious manner with the other components of the pharmaceutical composition in which it is contained.

A pharmaceutically effective amount includes an amount of the peptide that is sufficient to inhibit cell growth or proliferation, angiogenesis, or fibrosis. A pharmaceutically effective amount also includes an amount of the peptide that is sufficient to inhibit cell growth or proliferation of endothelial cells in vivo or in vitro. A pharmaceutically effective amount also includes an amount of the peptide that is sufficient to reduce collagen formation. In some instances, the concentration of the peptide in a liquid pharmaceutical formulation may be in the range of about 10 mg/ml to about 200 mg/ml, or about 25 mg/ml to about 175 mg/ml, or about 40-70 mg/ml, or about 40 to about 60 mg/ml, or ranges therein. For example, the formulation may have a concentration of about 20 mg/ml, 30 mg/ml, 40 mg/ml, 50 mg/ml, 60 mg/ml, 70 mg/ml, 80 mg/ml, 90 mg/ml, or 100 mg/ml. In some instances, the concentration of the peptide may be up to 50 mg/ml, up to 100 mg/ml, up to 150 mg/ml, or up to 200 mg/ml. In some instances, the amount of the peptide in a solid pharmaceutical formulation may be in the range of about 5 mg to 1 gram, or about 10 mg to 60 mg, or about 25 mg to 75 mg, or about 50 to 150 mg, or about 75 mg to 200 mg, or about 150 mg to 300 mg, or about 250 mg to 500 mg, or about 350 mg to 650 mg, or about 500 mg to 750 mg, or about 10 mg to 500 mg, or about 100 mg to 500 mg, or about 400 mg to 750 mg. For example, the formulation may have an amount of peptide of 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1 gram. In some instances, the amount of the peptide may be up to 100 mg, 150 mg, 200 mg, 250 mg, 300 mg, 350 mg, 400 mg, 450 mg, 500 mg, 550 mg, 600 mg, 650 mg, 700 mg, 800 mg, 900 mg, or 1000 mg. In some instances, the amount of the peptide in a semi-solid pharmaceutical formulation may be in the range of about 0.1% to 50%, or about 1% to 10%, or about 5% to 15%, or about 10% to 20%, or about 15% to 25%, or about 20% to 30%, or about 25% to 35%, or about 30% to 40%, or about 35% to 50%, or about 0.2% to 20%, or about 20% to 30%. For example, the formulation may have an amount of peptide of 0.1%, 0.2%, 0.5%, 0.8%, 1%, 1.5%, 2%, 5%, 10%, 25%, 40%, or 50%. In some instances, the formulation may have an amount of peptide up to about 0.1%, 0.2%, 0.5%, 0.8%, 1%, 1.5%, 2%, 5%, 10%, 25%, 40%, or 50%.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, for example, Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, orimmunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the peptides described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

The described compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like, may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active ingredient in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the peptides described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances and the like.

Compositions of the peptides described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the peptides described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the peptides described herein and a pharmaceutically acceptable carrier. As used herein, the term pharmaceutically acceptable salt refers to those salts of the peptides described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66: 1, which is incorporated herein by reference in its entirety, at least, for compositions taught therein.)

Administration of the peptides and compositions described herein, or pharmaceutically acceptable salts thereof, can be carried out using pharmaceutically effective amounts of the peptides and compositions described herein, or pharmaceutically acceptable salts thereof as described herein, for periods of time effective to treat a disorder. The effective amount of the peptides and compositions described herein, or pharmaceutically acceptable salts thereof as described herein, may be determined by one of ordinary skill in the art and includes exemplary dosage amounts for a mammal of from about 5 mg to 1 gram/kg of body weight of active peptide per day, which may be administered in a single dose or in the form of individual divided doses, such as from 2, 3, 4, 5, or 6 times per day. For example, the dosage amount can be from about 10 mg to 80 mg/kg of body weight of active peptide per day, about 400 mg to about 700 mg/kg of body weight of active compound per day, about 200 mg to about 800 mg/kg of body weight of active compound per day, about 500 mg to about 1 g/kg of body weight of active compound per day, about 100 mg to about 300 mg/kg of body weight of active compound per day, or about 800 mg to about 1000 mg/kg of body weight of active compound per day. In some aspects, the dosage amount can be up to about 100 mg/kg of body weight of active compound per day, about 200 mg/kg of body weight of active compound per day, about 400 mg/kg of body weight of active compound per day, about 600 mg/kg of body weight of active compound per day, about 800 mg/kg of body weight of active compound per day, or about 1000 mg/kg of body weight of active compound per day.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat or ameliorate cancer in a subject. Also provided are method to prevent or reduce the likelihood of cancer occurring in a subject. Also provided are methods of inhibiting cancer cell growth or proliferation in a subject, methods of inhibiting angiogenesis in a cell, and methods of inhibiting fibrosis in a tissue. The methods include administering to a subject an effective amount of one or more of the peptides or pharmaceutical compositions described herein, or a pharmaceutically acceptable salt or prodrug thereof. Effective amount, when used to describe an amount of compound in a method, refers to the amount of a compound that achieves the desired pharmacological effect or other biological effect. The peptides and compositions described herein, or pharmaceutically acceptable salts thereof, are useful for treating cancer in humans, including, without limitation, pediatric and geriatric populations, and in animals, such as for veterinary applications.

As used herein, subject means both mammals and non-mammals. Mammals include, for example, humans; non-human primates, such as apes and monkeys; cattle; horses; sheep; rats; dogs; cats; mice; pigs; and goats. Non-mammals include, for example, fish, amphibians, reptiles, and birds.

Optionally, the cancer is prostate cancer, bladder cancer, bone cancer, brain cancer, breast cancer, colon cancer, cervical cancer, endometrial cancer, fallopian tube cancer, gastrointestinal cancer, genitourinary cancer, head and neck cancer, leukemia, lung cancer, lymphoma, melanoma, liver cancer, ovarian cancer, pancreatic cancer, peritoneal cancer, prostate cancer, renal cancer, skin cancer, or testicular cancer. In some instances, the cancer expresses the Ang(1-7) receptor mas. In some cases, the mas receptor is overexpressed in the cancer.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

The methods of treating or preventing cancer in a subject can further comprise administering to the subject a therapeutic agent, radiation therapy, or a combination thereof. Thus, the provided compositions and methods can include one or more additional agents. The one or more additional agents and the peptides described herein, or pharmaceutically acceptable salts or prodrugs thereof, can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiandrogens (such as enzalutamide, flutamide, nilutamide, bicalutamide, and ARN-509); antiestrogens (such as tamoxifen); antimetabolites (such as fluorouracil (FU), 5-FU, methotrexate, floxuridine, interferon alpha-2B, glutamic acid, plicamycin, mercaptopurine, and 6-thioguanine); cytotoxic agents (such as carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (such as medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (such as mephalen, chlorambucil, mechlorethamine (nitrogen mustard) and thiotepa); steroids (such as bethamethasone sodium phosphate); Akt inhibitors; glucocorticoid receptor inhibitors (such as beclometasone, betamethasone, budesonide, ciclesonide, flunisolide, fluticasone, mifepristone, mometasone, and triamcinolone); and survival factor inhibitors (such as inhibitors of neurotrophins, cytokines, epidermal growth factor (EGF), platelet-derived growth factor (PDGF), fibroblast growth factor (FGF), insulin-like growth factor (IGF), heparin-binding epidermal growth factor (HB-EGF), vascular endothelial growth factor (VEGF), pigment epithelium-derived factor (PEDF), schwannoma-derived growth factor (SDGF), hepatocyte growth factor (HGF), transforming growth factor-α (TGF-α), transforming growth factor-β (TGF-β), bone morphogenetic proteins (such as BMP1-BMP15), growth differentiation factor-9 (GDF-9), granulocyte-colony stimulating factor (G-CSF), granulocyte-macrophage colony stimulating factor (GM-CSF), myostatin (GDF-8), erythropoietin (EPO), and thrombopoietin (TPO)).

Optionally, the one or more additional agents can include antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab' and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained. Exemplary antibodies include trastuzumab, alemtuzumab, ibritumomab, blinatumomab, bevacizumab, and cetuximab Optionally, the one or more additional agent can include cancer vaccines, such as, for example, sipuleucel-T (PROVENGE®, manufactured by Dendreon), which was approved in 2010 by the U.S. Federal and Drug Administration for use in some men with metastatic prostate cancer.

Any of the aforementioned additional agents can be used in any combination with the compositions described herein. Combinations are administered either concomitantly (such as as an admixture), separately but simultaneously (such as via separate intravenous lines into the same subject), or sequentially (such as one of the compounds or agents is given first followed by the second). Thus, the term combination is used to refer to concomitant, simultaneous, or sequential administration of two or more agents.

The methods and peptides as described herein are useful for both prophylactic and therapeutic treatment. For prophylactic use, a pharmaceutically effective amount of the peptides and compositions or pharmaceutically acceptable salts thereof as described herein are administered to a subject prior to onset (that is before obvious signs of cancer), during early onset (such as upon initial signs and symptoms of cancer), or after the development of cancer. Prophylactic administration can occur for several days to years prior to the manifestation of symptoms of cancer. Therapeutic treatment involves administering to a subject a pharmaceutically effective amount of the compounds and compositions or pharmaceutically acceptable salts thereof as described herein after cancer is diagnosed.

The peptides described herein are also useful in inhibiting Ang(1-7) receptor mas activity in a cell. The methods of inhibiting mas receptor activity in a cell include contacting the cell with an effective amount of one or more of the peptides as described herein. Optionally, the contacting is performed in vivo, such as, for example, wherein the cell is in a subject Optionally, the contacting is performed in vitro.

Figure 4:
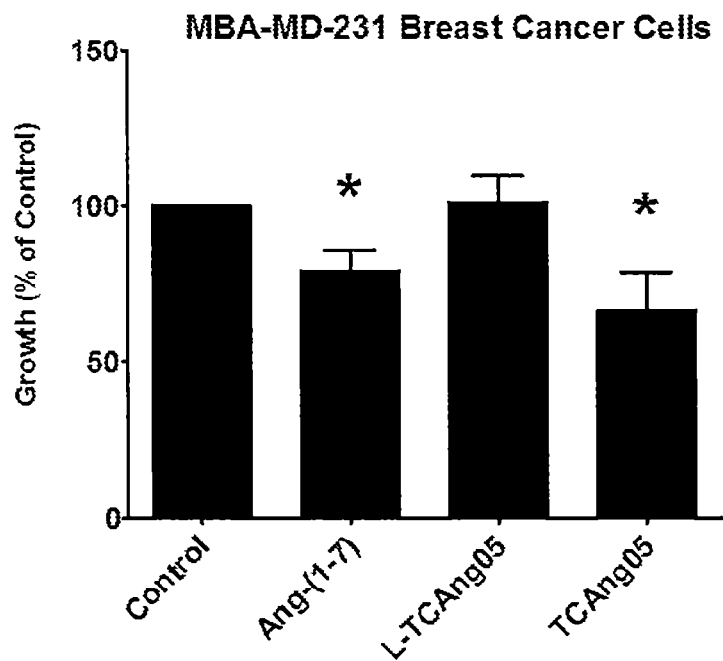
FIG. 4 shows a graph depicting growth inhibition observed in MDA-MB-231 human breast cancer cells treated with 100 nM of Ang-(1-7), a linear form of TCAng05 (L-TCAng05; SEQ ID NO:7), or TCAng05 according to one aspect. Subconfluent monolayers of actively growing cells were incubated for 7 to 10 days, and cell number was counted using a Nexelcom Cellometer. Ang-(1-7) was added daily due to its rapid degradation; analogs were added on Day 0. n=3-14 in duplicate, * denotes p<0.05.
Figure 5:
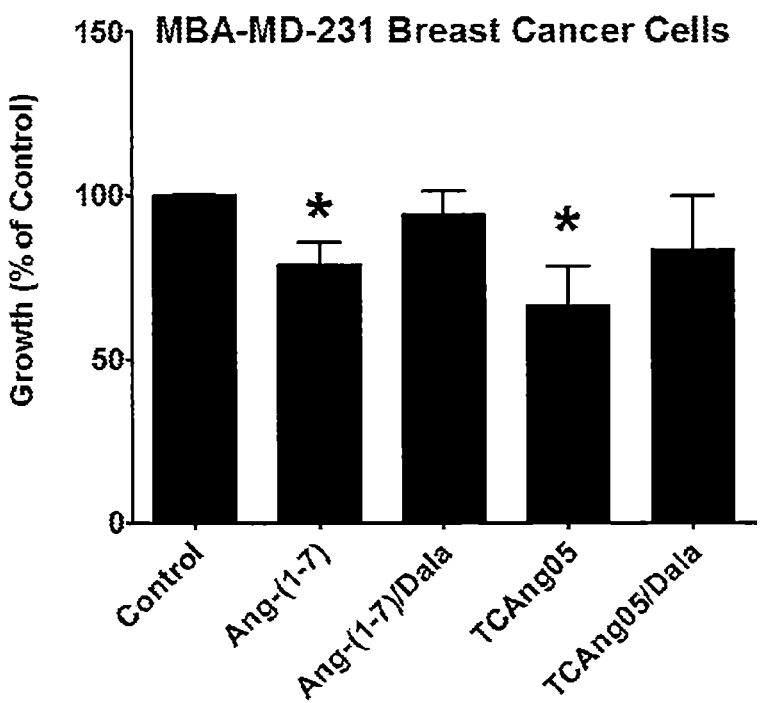
FIG. 5 shows a graph depicting growth inhibition observed in MDA-MB-231 human breast cancer cells treated with 100 nM of Ang-(1-7) (added daily) or TCAng05 in the presence or absence of 1 µM D-Alanine$^7$-Ang-(1-7) [Dala], a Ang-(1-7) receptor antagonist, according to one aspect. Subconfluent monolayers of actively growing cells were incubated for 7 to 10 days, and cell number was counted using a Nexelcom Cellometer. The results show that Ang(1-) and TCAng05 mediated growth inhibition acts via the Ang-(1-7) receptor mas. n=4-14 in duplicate, * denotes p<0.05.

Described herein is the use of Ang(1-7) peptide analogs to inhibit cancer growth. For example, referring now to FIG. 2 and FIG. 3 and Example 3, each of TCAng04 and TCAng05 significantly reduced the growth of both MDA-MB-231 breast cancer cells and A549 lung cancer cells. In contrast to Ang(1-7), which degrades rapidly in a cellular environment and, as such, required daily doses, the peptide analogs may be administered as a single dose, indicating the greater stability thereof. In one aspect, the cyclic structure of the peptide analogs increases their stability as compared to a linear peptide. For example, referring to FIG. 4 and Example 3, a linear form of TCAng05 (L-TCAng05) was ineffective in reducing MDA-MB-231 cell growth while the fully cyclized form of TCAng05 reduced growth. In some instances, the peptide analogs bind to the Ang(1-7) receptor mas present on tumor cells to impact regulation of cell growth and proliferation. For example, the inhibition of growth by either Ang-(1-7) or TCAng05 may be blocked by the Ang-(1-7) receptor antagonist D-Ala$^7$-Ang-(1-7) [Dala], as shown in FIG. 5 and Example 3. Thus, in some instances, the Ang(1-7) peptide analogs described herein inhibit cell growth in vitro and, in some instances, the response is mediated by the selective Ang-(1-7) receptor mas.

Figure 6A:
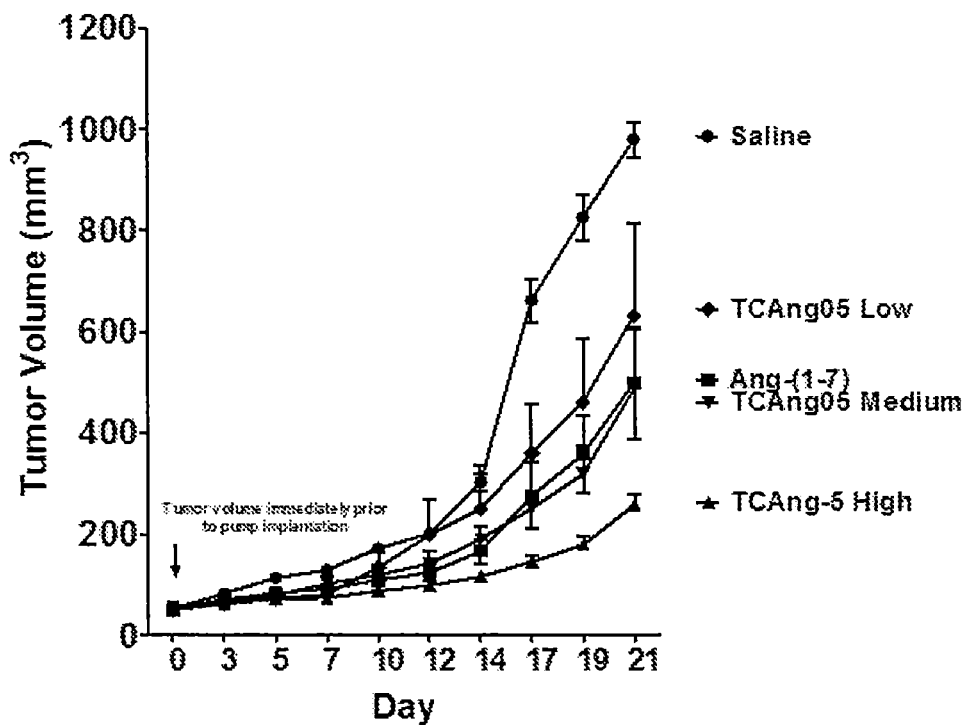
FIG. 6A shows a graph depicting inhibition of in vivo tumor growth (volume) by TCAng05 administered subcutaneously in an orthotopic model of human breast cancer, according to one aspect. 4T1 mouse breast cancer cells ($2.5 \times 10^5$ in saline) were injected into the $4^{th}$ mammary fat pad of BALB/c mice, and tumor size was measured every 3 days and used to calculate tumor volume. Treatment was started when the tumors reached a size of 100 mm³ (Day 0) by insertion of osmotic minipumps into the subscapular space. Treatment groups (n=4 animals/group) were saline, 24 µg/kg/h Ang-(1-7), 6 µg/kg/h TCAng05 (low), 12 µg/kg/h TCAng05 (medium) or 24 µg/kg/h TCAng05 (high). At the time of sacrifice (Day 21), the tumors were weighed and differences in tumor weight were compared.
Figure 6B:
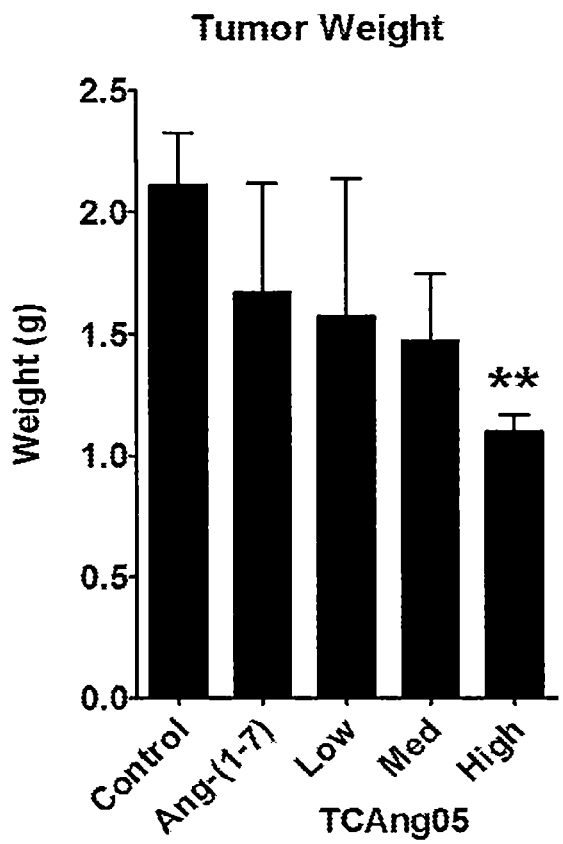
FIG. 6B shows a graphs illustrating impact on tumor weight (** denotes $p<0.01$)
Figure 6C:
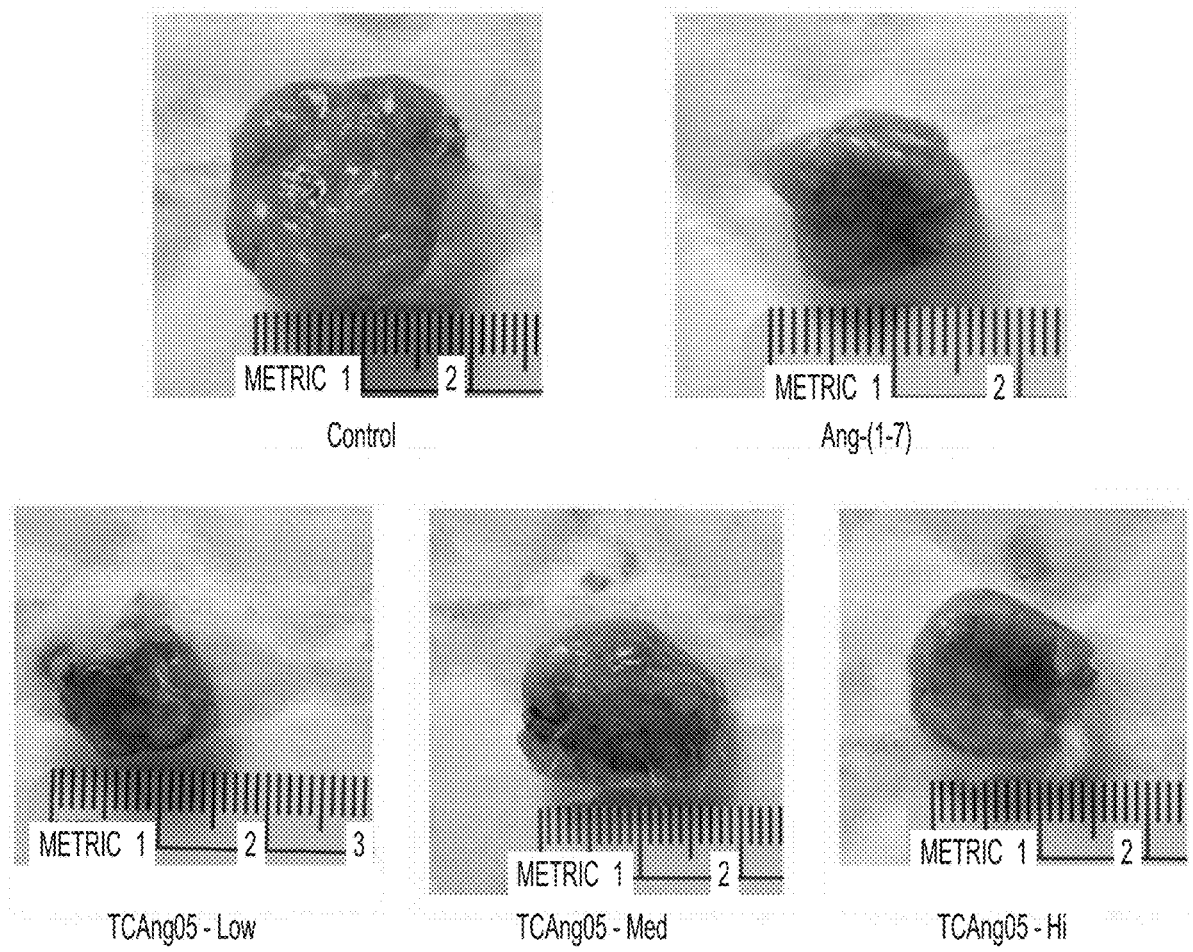
FIG. 6C shows representative pictures of tumors. Treatment with Ang-(1-7) reduced tumor size 50%. TCAng05 caused a dose-dependent reduction in tumor size, with the high dose causing a reduction in tumor volume of 74% compared to untreated (saline) mice, demonstrating that TCAng05 reduces tumor growth. Tumor weight was also reduced by treatment with TCAng05, by 48% at the highest concentration used.
Figure 7A:
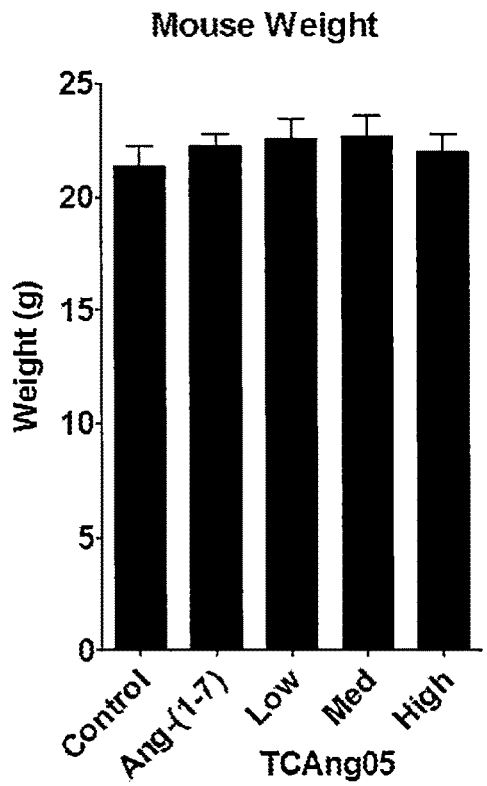
FIG. 7A-FIG. 7C show graphs depicting weight measurements for the sacrificed mice treated in Example 4 and described in FIGS. 6A-6C, as well as their hearts and kidneys, respectively, in comparison to untreated (saline) mice, according to one aspect. No change in weight was observed, indicating that Ang-(1-7) and the peptide analogs were well-tolerated by the mice.
Figure 7B:
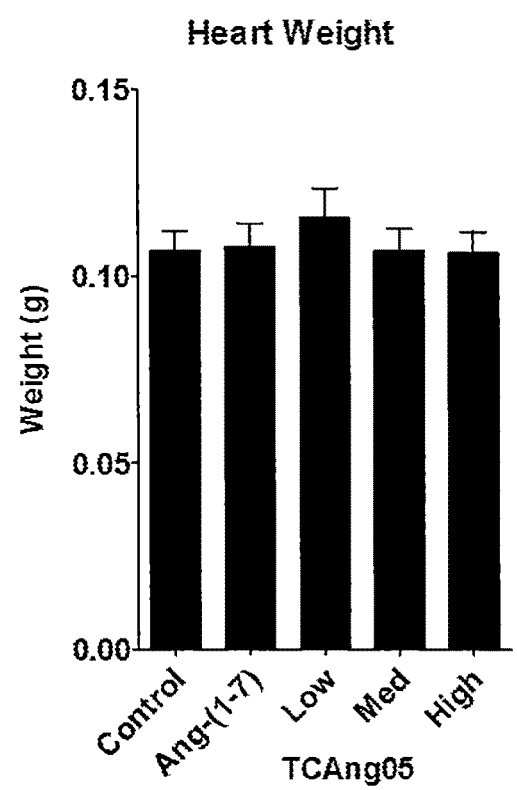
Figure 7C:
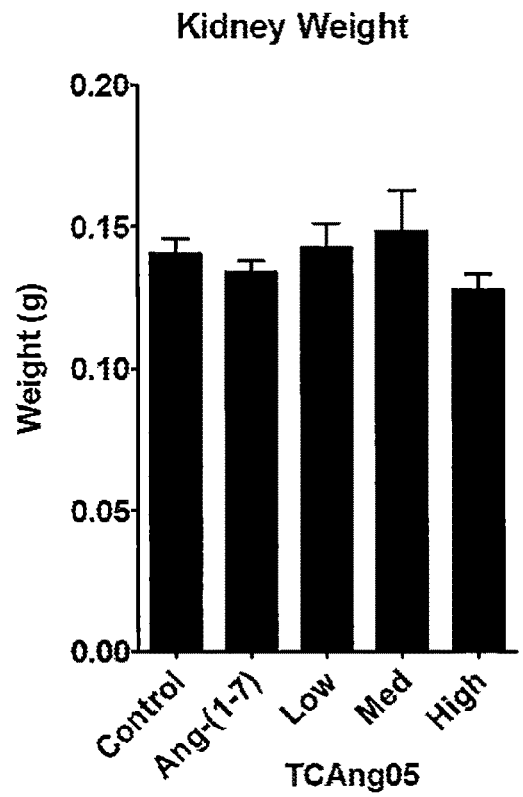

The ability of Ang(1-7) peptide analogs as described herein, such as TCAng05, to inhibit tumor growth in vivo may be shown in an orthotopic model of human breast cancer, using 4T1 breast cancer cells, as described in Example 4. For example, A4T1 cells may be injected into the mammary fat pad of BALB/C mice (2.5×10$^5$ cells in saline). Once the tumors reach a desired size, such as, for example, 100 mm$^3$, primed osmotic mini-pumps may be implanted into the subcutaneous space on the back of each mouse to deliver treatment. As shown in FIG. 6A, tumors in mice with no treatment (saline) continued to growth until the mice were sacrificed (final size of 980.1±35.0 mm$^3$). In one instance, daily treatment with Ang-(1-7) (24 µg/kg/h) may reduce tumor size about 50% (final size 495.5±110.8 mm$^3$). In some instances, an Ang(1-7) analog (TCAng05) may cause a dose-dependent reduction in tumor size, with a high dose (24 µg/kg/h) reducing tumor volume about 74% (final size 259.1±19.2 mm$^3$) compared to untreated mice (treated with saline). In some instances, low (6 µg/kg/h) and medium (12 µg/kg/h) doses may not significantly impact cell proliferation. In some instances, tumor weight may be reduced, as shown in FIG. 6B, as well as overall visually apparent size, as shown in FIG. 6C. Administration of Ang(1-7) peptide analogs, like administration of Ang(1-7) peptide, may be well tolerated by subjects. For example, as shown in FIGS. 7A-7C and described in Example 4, there was no change in the weight, heart size, or kidney size of treated subjects. Thus, Ang(1-7) peptide analogs as described herein, such as TCAng05, may be effective in inhibiting cancer cell proliferation and tumor growth when administered by injection.

Figure 8A:
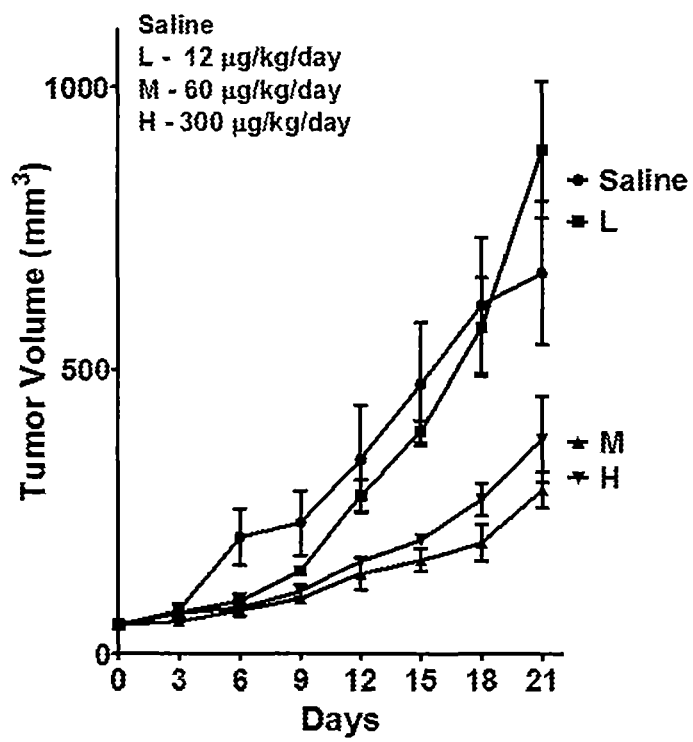
FIG. 8A shows a graph depicting inhibition of in vivo tumor growth (volume) by TCAng05 administered orally in the orthotopic model of human breast cancer described in Example 5, according to one aspect. Treatment groups (n=3-4 animals/group) were saline, 12 µg/kg/day TCAng05 (low), 60 µg/kg/day TCAng05 (medium) or 300 µg/kg/day TCAng05 (high). At the time of sacrifice (Day 21), the tumors were weighed and differences in tumor weight were compared.
Figure 8B:
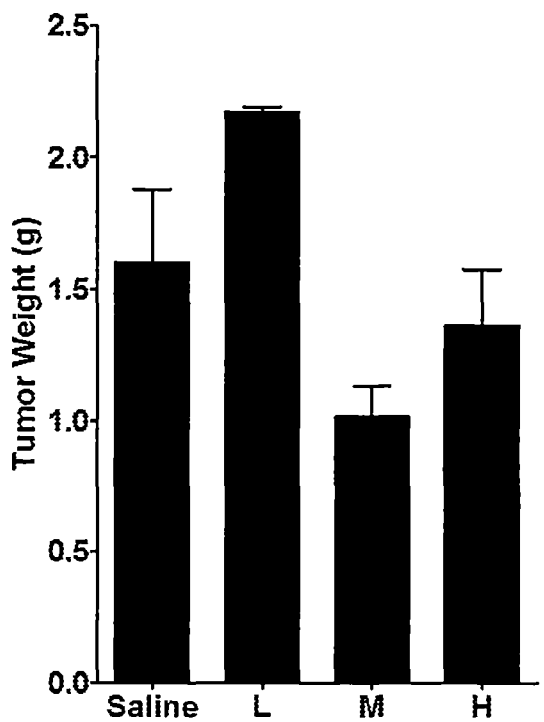
FIG. 8B shows a graphs illustrating reduction in tumor weight with treatment. TCAng05 caused a reduction in tumor size; the medium dose reduced tumor volume 57% and the high dose reduced tumor size 43% compared to untreated (saline) mice. Tumor weight was also reduced by treatment with TCAng05, as shown in FIG. 8B.
Figure 9A:
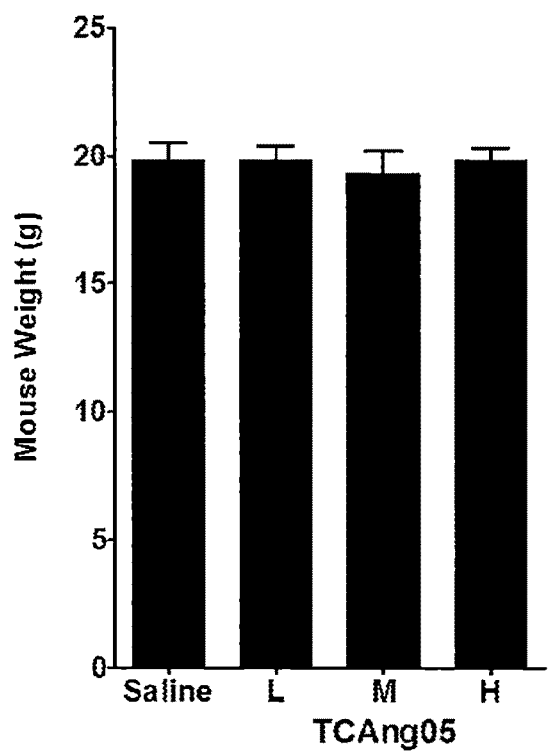
FIG. 9A-FIG. 9C show graphs depicting weight measurements for the sacrificed mice treated in Example 5 and described in FIGS. 8A-8B, as well as their hearts and kidneys, respectively, in comparison to untreated (saline) mice, according to one aspect. No change in weight was observed, indicating that Ang-(1-7) and the peptide analogs were well-tolerated by the mice.
Figure 9B:
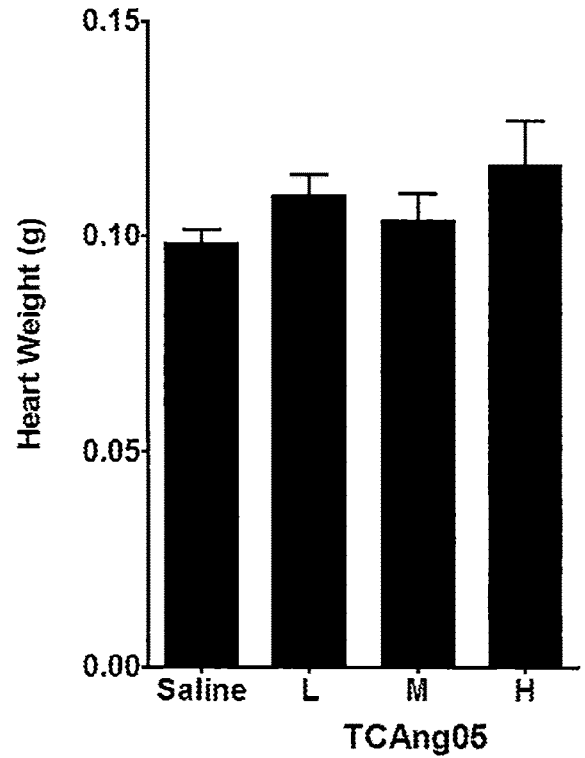
Figure 9C:
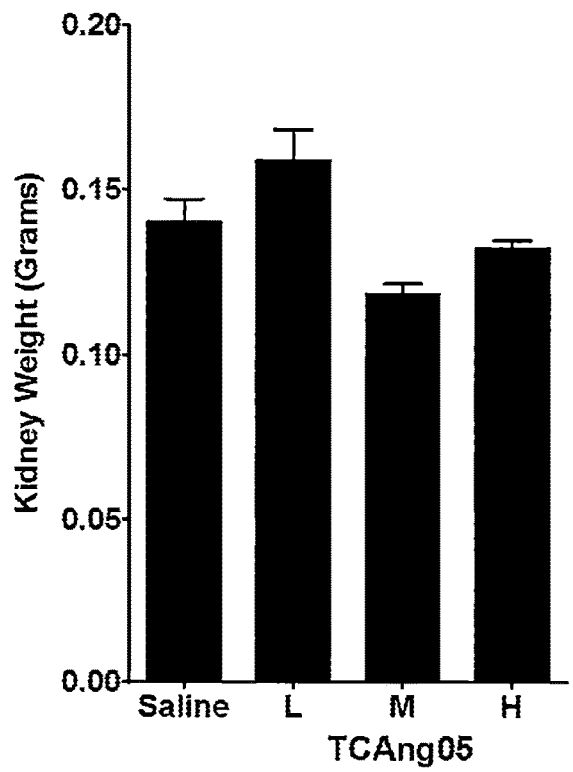

In some instances, Ang(1-7) peptide analogs as described herein may be effective in inhibiting cancer cell proliferation and tumor growth when administered orally. The ability of Ang(1-7) peptide analogs as described herein, such as TCAng05, to inhibit tumor growth in vivo may be shown in an orthotopic model of human breast cancer, using 4T1 breast cancer cells, as described in Example 5. For example, instead of injecting the peptide analogs, the mice may receive a daily gavage of the analogs. As shown in FIG. 8A, tumors in mice with no treatment (saline only) may grow until the mice are sacrificed (final size 671.2±127.2 mm$^3$). In some instances, oral treatment with a peptide analog, such as TCAng05, at either medium (60 µg/kg/day) or high (300 µg/kg/day) doses may reduce tumor volume by about 56.8% (final size 289.7±64.2 mm$^3$) and about 43.6% (final size 378.3±151.2 mm$^3$), respectively. In some instances, low (12 µg/kg/day) doses may not significantly impact cell proliferation. For example, as shown in FIG. 8B, tumor weight may also be reduced by treatment with either medium or high oral doses of peptide analogs such as TCAng05. In contrast, treatment with peptide analogs such as TCAng05 may have no impact on total weight, heart weight, or kidney weight of the treated subject, as shown in FIGS. 9A-9C. Thus, oral administration of Ang(1-7) peptide analogs may be well tolerated by subjects.

Figure 10:
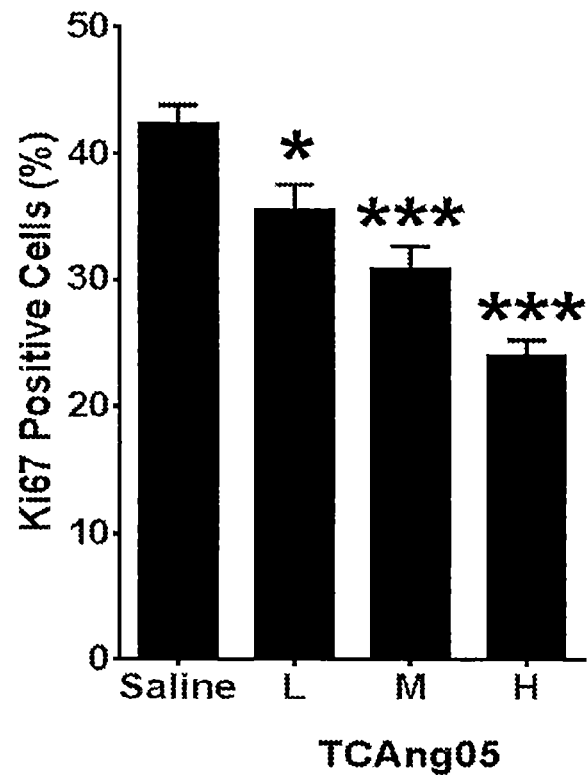
FIG. 10 shows a graph depicting a reduction in tumor cell proliferation observed in the mice treated orally with TCAng05 as described in Examples 5 and 6 and FIGS. 8A-9C based on immunohistochemical analysis using an antibody that specifically binds Ki67, which labels cells that are actively proliferating, according to one aspect. The number of immunopositive cells is expressed as a percentage of the total cell number examined (100 cells counted from each tissue site within a tumor section). Oral TCAng05 administration caused a reduction in Ki67-positive cells, indicating that the Ang-(1-7) analog reduces tumor proliferation, similar to data in lung, prostate and breast tumors with native Ang-(1-7). (n=5. * denotes $p<0.05$ and *** denotes $p<0.001$.)
Figure 11:
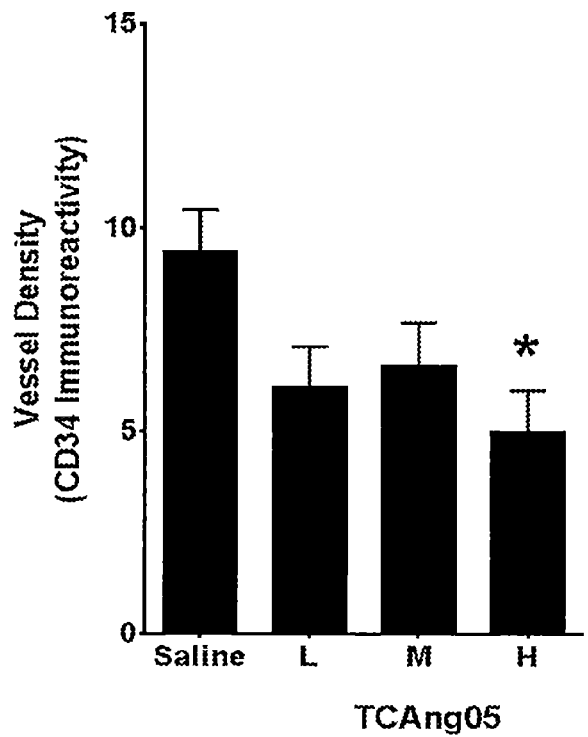
FIG. 11 shows a graph depicting a reduction in the number of blood vessels observed in the mice treated orally with TCAng05 as described in Examples 5 and 6 and FIGS. 8A-9C based on immunohistochemical analysis using an antibody that specifically binds CD34, which labels endothelial cells, according to one aspect. Blood vessels were visualized by the presence of CD34-immunostained endothelial cells and identified by morphology, as vessels cut in cross-section with visible lumens or vessels cut longitudinally with tube-like morphology. The number of vessels was expressed as the average of 6 fields (0.3 mm²) selected per tumor. Oral TCAng05 administration caused a reduction in blood vessels, indicating that the Ang-(1-7) analog reduces angiogenesis, similar to data in lung, prostate and breast tumors with native Ang-(1-7). (n=5. * denotes $p<0.05$.)
Figure 12:
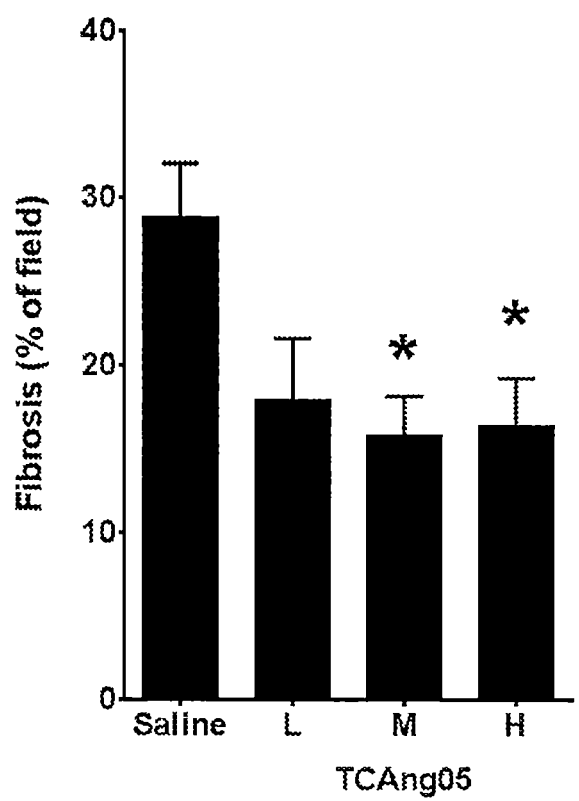
FIG. 12 shows a graph depicting a reduction in interstitial fibrosis observed in the mice treated orally with TCAng05 as described in Examples 5 and 6 and FIGS. 8A-9C based on collagen staining using Picrosirius red, according to one aspect. Interstitial fibrosis was expressed as a percentage of reactive fibers/field (four fields/tumor section/mouse). Oral TCAng05 caused a reduction in interstitial fibrosis, indicating that the Ang-(1-7) analog reduces angiogenesis, similar to data in breast tumors with native Ang-(1-7). (n=5. * denotes $p<0.05$.)

In some instances, the molecular mechanism of action for the Ang(1-7) peptide analogs impact cell proliferation, angiogenesis, and collagen formation. Example 6 describes analysis of the molecular mechanisms of Ang(1-7) peptide analog activity. Specifically, immunohistochemical analysis was performed on formalin-fixed, paraffin-embedded tumor tissue samples from the orally treated mice described in Example 3. For example, tumor sections may be stained with an antibody to Ki67 as a measure of cell proliferation. In some instances, as shown in FIG. 10, administration of TCAng05 may cause a dose-dependent reduction in Ki67 immunoreactivity, suggesting that the analog reduced the proliferation of tumor cells, as has been previously observed with Ang-(1-7) in human prostate tumors in mice as described by Krishnan et al., Prostate 2013; 73:60-70. As shown in FIG. 11, administration of Ang(1-7) peptide analogs, such as TCAng05, to mice with breast tumors caused a significant reduction in the density of blood vessels, measured by labeling endothelial cells lining blood vessels with an antibody to CD34, suggesting that, in some instances, the analogs may reduce angiogenesis to decrease tumor size. In some instances, this impact on cell proliferation is consistent with the observation in mice with human lung tumors or human prostate tumors, that Ang-(1-7) reduce angiogenesis as described by Soto-Pantoj a et al. Mol Cancer Ther 2009; 8:1676-83 and Krishnan et al., Prostate 2013; 73:60-70). In some instances, this impact on cell proliferation is consistent with the reduction in the pro-angiogenic peptide platelet-derived growth factor (PDGF) observed in patients with solid tumors treated with Ang-(1-7) (Petty et al., BMC Cancer 2012; 12:404). In some instances, native Ang-(1-7) reduces fibrosis by reducing the proliferation of cancer-associated fibroblasts and their production of pro-fibrotic proteins in mice with human breast tumors, as described by Cook et al., Cancer Research 2010; 70:8319-28. In some instances, as shown in FIG. 12, collagen staining with Picrosirius red was reduced by oral administration of TCAng05, demonstrating that the peptide analogs, such as TCAng05, may reduce fibrosis similar to the native peptide. Thus, in some instances, oral administration of TCAng05 to mice with breast tumors reduced tumor size, by decreasing tumor cell proliferation, angiogenesis, and fibrosis, as previously observed with the native Ang-(1-7).

In some instances, Ang(1-7) peptides having a cyclic structure may effectively inhibit cell proliferation or cell growth. An exemplary series of described analogs are shown in Table 1. In some instances, peptide analogs may have substitutions of single amino acid residues, deletion of specific residues, and/or substitution of key residues.

Figure 13:
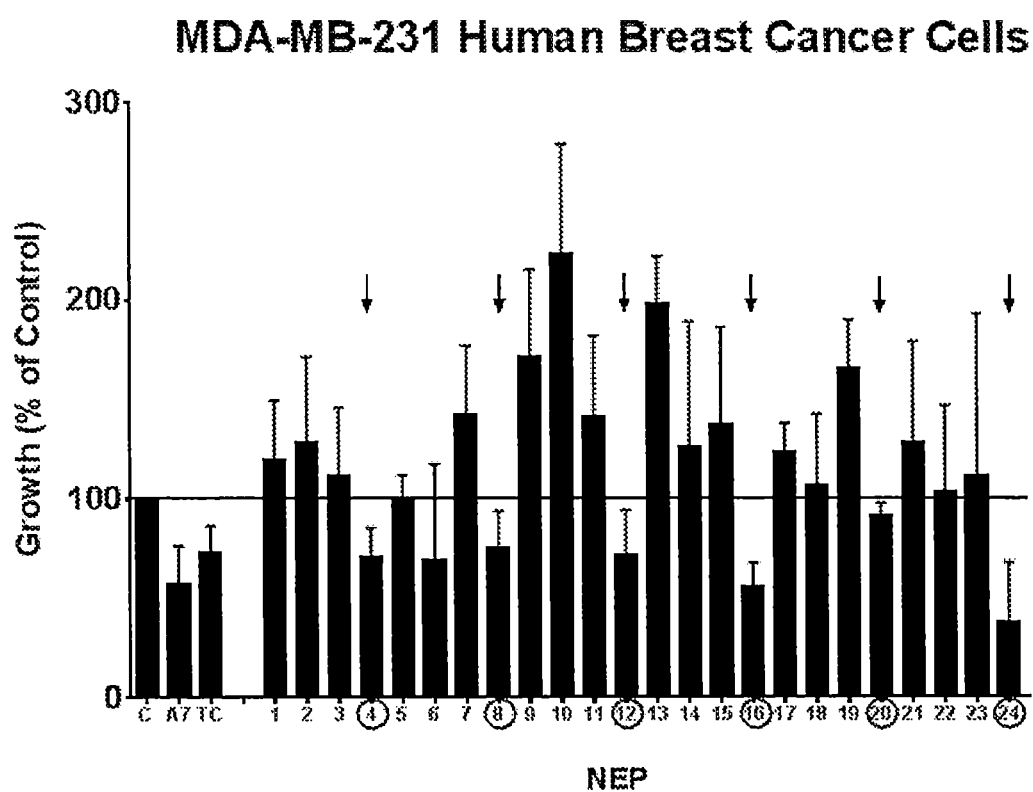
FIG. 13 shows a graph depicting cell growth inhibition of MDA-MB-231 human breast cancer cells incubated with 100 nM of Ang-(1-7), analog TCAng05, or one of analogs NEP1-24, according to one aspect. Subconfluent monolayers of actively growing cells were incubated for 8 to 10 days. Ang-(1-7) was added daily as it is rapidly degraded while TCAng05 and all other analogs were added twice weekly, at the time the cells were fed. Cell number was subsequently counted. (C, Control; A7, Ang-(1-7); TC, TCAng05. n=2-4 in triplicate.) Both Ang-(1-7) and TCAng05 significantly reduced cell growth (43.3±9.8% and 27.3±9.8%, respectively). Analogs NEP4, NEP8, NEP12, NEP16, NEP20, and NEP24 reduced cell growth comparably to Ang-(1-7) and TCAng05.

In some instances, the ability of Ang(1-7) analogs to impact cell growth may be assessed in vitro using human breast cancer cells. For example, as shown in FIG. 13 and described in Example 7, six analogs inhibited breast cancer cell growth similar to Ang-(1-7) or TCAng05. In some instances, any one of the following peptide analogs may inhibit cell growth to a similar extent as Ang-(1-7) or TCAng05: (i) a peptide analog in which isoleucine at $R^6$ in Z is replaced with alanine, such as in analog NEP4 (SEQ ID NO:11); (ii) a peptide analog that does not include D-Valine (dV) and D-Proline (dP) as group $Y^1$, such as in analog NEP8 (SEQ ID NO:15); (iii) a peptide analog in which isoleucine at $R^6$ in Z is replaced with leucine, such as in analog NEP12 (SEQ ID NO:19); (iv) a peptide analog in which norleucine at $R^1$ is modified to contain an amide (H2N), such as in analog NEP16 (SEQ ID NO:23); (v) a peptide analog in which lysine at $R^9$ is modified with an N-methyl group, such as in analog NEP20 (SEQ ID NO:27); and (vi) a peptide analog in which $R^9$ is 2,4-diaminobutyric acid prior to $Y^1$ of D-valine-D-proline residues, such as in analog NEP24 (SEQ ID NO:31).

V. Kits

Also provided herein are kits for treating or preventing cancer in a subject. In one aspect, the kits are for treating cancer in a subject. In another aspect, the kits are for use in preventing cancer in a subject. A kit can include any of the peptides or compositions described herein, or pharmaceutically acceptable salts thereof. For example, a kit can include one or more peptides Formula I or pharmaceutically acceptable salts thereof. A kit can further include one or more additional agents, such as a chemotherapeutic agent. A kit can include an oral formulation of any of the peptides or compositions described herein. A kit can additionally include directions for use of the kit (such as instructions for treating a subject), a container, a means for administering the compounds or compositions, and/or a carrier. Kits can include single doses or multiple doses (such as, for example, in a blister pack or a multi-dose volume vial). Kits can include can include means for administration (such as a delivery device like a syringe, a nebulizer, or an inhaler), or the like.

While aspects of the invention will now be described in connection with certain preferred embodiments in the following examples and with reference to the attached figures so that aspects thereof may be more fully understood and appreciated, it is not intended to limit the invention to these particular embodiments. On the contrary, this application is intended to cover all alternatives, modifications and equivalents as may be included within the scope of the invention as defined by the appended claims. Thus, the following examples, which include preferred embodiments, will serve to illustrate the practice of the described compositions, methods, and kits, it being understood that the particulars shown are by way of example and for purposes of illustrative discussion of preferred embodiments only, and are presented in the cause of providing what is believed to be useful and readily understood description of formulation procedures, as well as of the principles and conceptual aspects of the invention. It will be evident to those skilled in the art that the invention described herein may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

All printed patents and publications referred to in this application are hereby incorporated by reference herein in their entirety.

EXAMPLES

Example 1

Synthesis of Ang-(1-7) Analogs

Reagents and solvents were purchased from commercial suppliers and used as received unless noted otherwise.

Peptide TCAng05 (SEQ ID NO:6) was synthesized according to the method depicted in Scheme 2. Procedures for each step of the synthesis are provided below.

Scheme 2:

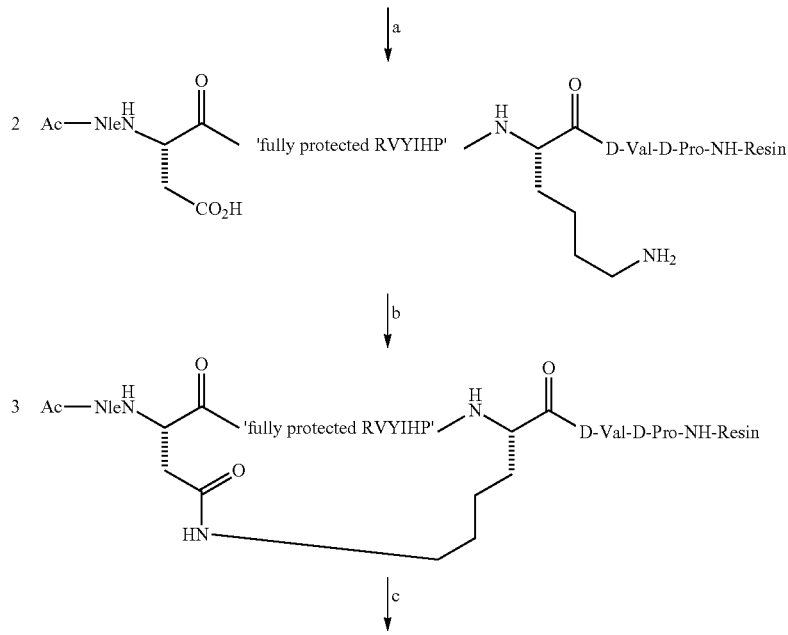

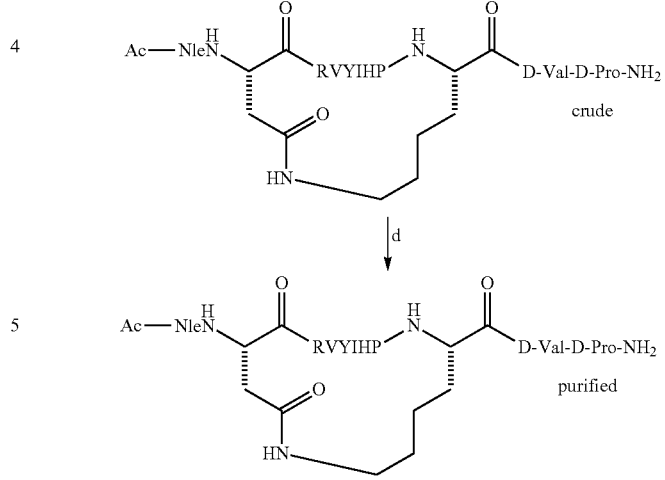

Reagents and conditions: (a) TFA; (b) lyophilization, 10X DIEA + 4X PyBOP in DMF, overnight; (c) lyophilization, TFA; (d) high performance liquid chromatography (HPLC).

The starting peptide (1) is fully protected on all the chemically reactive groups. In one specific example, the epsilon amino of the aspartic acid, which corresponds to position $R^2$ of Z in Formula I, is protected with a 2-phenylisopropyloxy (O-2-PhiPr) group, and the beta carboxylic of the lysine at $R^9$ with a 4-methyltrityl (Mtt) group. Deprotection with TFA is then performed to remove the protecting groups on the epsilon amino of the lysine at $R^2$ and beta carboxylic of the aspartic acid at $R^9$, which are to be the points of cyclization. This yields the partially protected peptide (2), which is then lyophilized. The cyclization reaction is performed in dimethylformamide (DMF) overnight in presence of 10 molar excess of di-isopropylethylamine (DIEA) (tertiary base) and 4 molar excess of benzotriazol-1-yl-oxytripyrrolidinophosphonium hexafluorophosphate (PyBOP) (activating agent). The reaction is monitored by liquid chromatograph-mass spectrometry (LC-MS) until completion, yielding the fully protected cyclized peptide (3) and then is diluted 1 to 8 in 30% water-acetonitrile and lyophilized. A final deprotection step is performed with TFA. Crude reaction material was purified by HPLC to generate TCAng05 (5) and characterized by mass spectrometry.

Example 2

Stability Assessment of Ang-(1-7) Analogs

The stability of the Ang(1-7) peptide analog TCAng04 (SEQ ID NO:5) was assessed in rat plasma. The peptide was incubated with rat plasma at 37° C. for 60 min (left) or 125 hours (right). The concentration of TCAng04 and Ang-(1-7) was determined by HPLC using verified standards. Ang-(1-7) was rapidly degraded following incubation in rat plasma with a half-life of about 30 min, similar to the pharmacokinetics observed in two clinical trials (FIG. 1B) (see Rodgers et al. Cancer Chemother Pharmacol 2006; 57:559-68; and Petty et al. Clinical Cancer Research 2009; 15:7398-404). Conversely, TCAng04 was stable under the same conditions, with a half-life in rat plasma of approximately 50 hours.

Example 3

In Vitro Inhibition of Cancer Cell Growth

Figure 2:
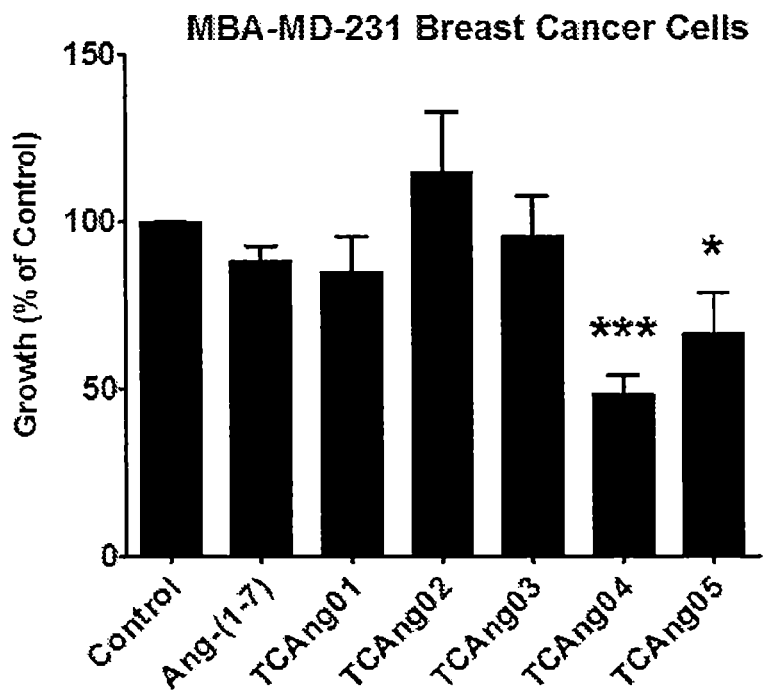
FIG. 2 shows a graph depicting growth inhibition observed in MDA-MB-231 human breast cancer cells treated with 100 nM of Ang-(1-7) or TCAng01-TCAng05 in accordance with one aspect. Subconfluent monolayers of actively growing cells were incubated for 7 to 10 days, and cell number was counted using a Nexelcom Cellometer. Ang-(1-7) was added daily due to its rapid degradation; analogs were added on Day 0. n=4-14 in duplicate, * denotes p<0.05 and *** denotes p<0.001.
Figure 3:
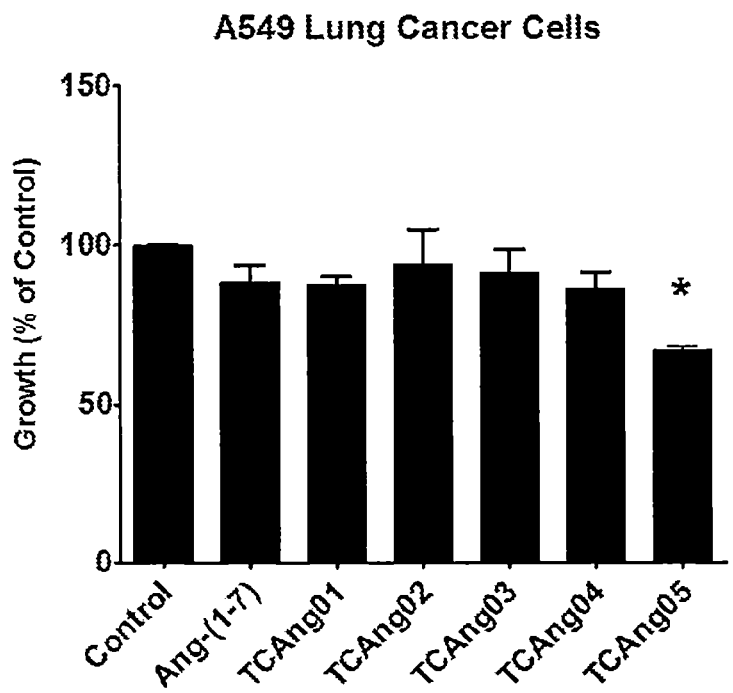
FIG. 3 shows a graph depicting growth inhibition observed in A549 human lung cancer cells treated with 100 nM of Ang-(1-7) or TCAng01-TCAng05 in accordance with one aspect. Subconfluent monolayers of actively growing cells were incubated for 7 to 10 days, and cell number was counted using a Nexelcom Cellometer. Ang-(1-7) was added daily due to its rapid degradation; analogs were added on Day 0. n=3-14 in duplicate, * denotes p<0.05.

To determine the effect of the peptide analogs on tumor cell growth, 100 nM Ang-(1-7) or analogs TCAng01-TCAng05 (SEQ ID NOs:2-6) were incubated with subconfluent monolayers of actively growing A549 human lung cancer cells or MDA-MB-231 human breast cancer cells in 24-well cluster plates for 6 to 10 days or 7 to 10 days. Assays were performed in duplicate for 4-14 replicates or 3-14 replicates, respectively. Cell number was counted using a Nexelcom Cellometer. As shown in FIG. 2 and FIG. 3, both TCAng04 and TCAng05 significantly reduced the growth of both MDA-MB-231 and A549 cells (by 51.5±5.4% and 33.7±12.3%), respectively, while the other three analogs were ineffective at reducing cell growth. Ang-(1-7) also did not inhibit breast cancer cell growth as it is rapidly degraded and was only added on Day 1. Ang-(1-7) does inhibit the growth of human breast cancer cells (by 42.9±5.2%, n=6, over 6-10 days) and human lung cancer cells (by 53.1±7.1%, n=12, over 7-10 days) if it is added daily, as shown in FIG. 2 and FIG. 3. This is in contrast to the comparable effectiveness of a single dose of TCAng04 or TCAng05 in reducing cell growth, demonstrating the extended half-life of the peptide analogs.

A linear form of TCAng05 (L-TCAng05; SEQ ID NO:7) was tested to determine the influence of cyclization on the stability of the peptide. Subconfluent monolayers of MDA-MB-231 human breast cancer cells were incubated with 100 nM of Ang-(1-7), L-TCAng05, or TCAng05 for 7 to 10 days and cell number was counted using a Nexelcom Cellometer. Assays were performed in duplicate for 3-14 replicates. Ang-(1-7) was added daily, due to its rapid degradation. As shown in FIG. 4, the linear L-TCAng05 (SEQ ID NO:7) was found to be ineffective in reducing MDA-MB-231 cell growth while the fully cyclized form of TCAng05 reduced growth, indicating that the cyclized form of TCAng05 is necessary to inhibit cancer cell growth.

Similar assays were performed to assess whether inhibition of cell growth by TCAng05 was mediated by the Ang-(1-7) receptor mas. Subconfluent monolayers of MDA-MB-231 human breast cancer cells were incubated with 100 nM of Ang-(1-7), added daily, or TCAng05, in the presence or absence of 1 μM Ang-(1-7) receptor antagonist D-Alanine[7]-Ang-(1-7) [Dala] for 7 to 10 days and cell number was counted using a Nexelcom Cellometer. Assays were performed in duplicate for 4-14 replicates. As shown in FIG. 5, the inhibition of growth by either Ang-(1-7) or TCAng05 was blocked by Dala, showing that the response was selectively mediated by the Ang-(1-7) receptor mas.

Example 4

In Vivo Inhibition of Tumor Growth by Subcutaneous Administration

The ability of TCAng05 to inhibit tumor growth in vivo was measured in an orthotopic model of human breast cancer, using 4T1 breast cancer cells. 4T1 cells ($2.5 \times 10^5$ in saline) were injected into the $4^{th}$ mammary fat pad of BALB/C mice. Tumor size was measured every 3 days using a caliper and tumor volume was calculated using the formula for a semi-ellipsoid. The tumors were allowed to grow until they reached a size of 100 mm³, at which point subcutaneous treatment was started (Day 0). Primed osmotic mini-pumps were implanted into the subcutaneous space on the back of each mouse to deliver either saline, 24 µg/kg/h Ang-(1-7), 6 µg/kg/h TCAng05 (low), 12 µg/kg/h TCAng05 (medium), or 24 µg/kg/h TCAng05 (high). Mice were sacrificed on Day 21 of treatment. Five animals were used per treatment group. As shown in FIG. 6A, tumors in mice with no treatment (saline) continued to growth until the mice were sacrificed at Day 19, reaching a final size of 980.1±35.0 mm³. Treatment with Ang-(1-7) reduced tumor size 50%, to a final size of 495.5±110.8 mm³. TCAng05 caused a dose-dependent reduction in tumor size, with the high dose reducing tumor volume to 259.1±19.2 mm³, a reduction of 74% compared to untreated mice, treated with saline. At the time of sacrifice, the mice were weighed and the tumors, heart and kidneys were weighed. Tumor weight was reduced, as shown in FIG. 6B. Representative pictures of tumors from each treatment group are shown in FIG. 6C. As shown in FIGS. 7A-7C, there was no change in the weight of the mice, the size of their hearts or the size of their kidneys, indicating that Ang-(1-7), and the peptide analogs were well-tolerated by the mice.

Example 5

In Vivo Inhibition of Tumor Growth by Oral Administration

The oral efficacy of TCAng05 to inhibit tumor growth in vivo was also measured using the orthotopic model of human breast cancer described in Example 4. 4T1 breast cancer cells were injected into the mammary fat pad of BALB/C mice ($2.5 \times 10^5$ cells in saline). Tumor size was measured every 3 days using a caliper and tumor volume was calculated using the formula for a semi-ellipsoid. The tumors were allowed to grow until they reached a size of 100 mm³, at which point treatment was started (Day 0). Mice received daily gavage of TCAng05 at one of three concentrations: 12 µg/kg/day (Low), 60 µg/kg/day (Medium), or 300 µg/kg/day (High). Mice were sacrificed on Day 21 of treatment. Treatment groups contained 3-4 animals. As shown in FIG. 8A, tumors in mice with no treatment continued to grow until the mice were sacrificed at Day 19, at which time the tumors reached a size of 671.2±127.2 mm³. Oral treatment with TCAng05 at either the medium or high dose reduced tumor volume, by 56.8% and 43.6%, respectively, to final tumor volumes of 289.7±64.2 mm³ and 378.3±151.2 mm³ (n=3 to 4). At the time of sacrifice, the tumors were weighed. As shown in FIG. 8B, tumor weight was also reduced by treatment with either the medium or high of oral TCAng05. In contrast, there was no effect of TCAng05 on mouse weight, heart weight or kidney weight, as shown in FIGS. 9A-9C, indicating that oral administration of the Ang-(1-7) analog was also well-tolerated by the mice.

Example 6

Molecular Mechanism of Efficacy

To identify the molecular mechanisms for the reduction in tumor weight, tumors from mice that received oral TCAng05 (described in Example 5) were assessed for cell markers associated with cell proliferation, angiogenesis, and fibrosis. Tumors were fixed in 4% formalin, embedded in paraffin, sectioned at 5 microns, and analyzed by immunohistochemistry. Tumor tissue sections were visualized using a Leica DM microscope (Leica Microsystems, Bannockburn, Ill.) with the Simple PCI Version 6.0 computer-assisted imaging software (Hamamatsu Corporation, Sewickley, Pa.) and photographed with the QImaging Retiga 1300R Camera (QImaging Co. Surey, BC, Canada). The number of immunopositive cells is expressed as a percentage of the total cell number examined (100 cells counted from each tissue site within a tumor section).

Tumor sections were stained with an antibody specific for Ki67 to measure cell proliferation. As shown in FIG. 10, administration of TCAng05 caused a dose-dependent reduction in Ki67 immunoreactivity, suggesting that the analog reduced the proliferation of tumor cells, as has been previously observed with Ang-(1-7) in human prostate tumors in mice (Krishnan et al., Prostate 2013; 73:60-70).

Tumor sections were stained with an antibody specific for CD34 to label endothelial cells lining blood vessels and measure the density of blood vessels. As shown in FIG. 11, administration of TCAng05 caused a significant reduction in the density of blood vessels, suggesting that the analog reduces angiogenesis to decrease tumor size. In previous studies with orthotopic models, Ang-(1-7) reduced angiogenesis in mice with human lung tumors or human prostate tumors (Soto-Pantoj a et al., Mol Cancer Ther 2009; 8:1676-83; Krishnan et al., Prostate 2013; 73:60-70). This is in agreement with a reduction in the pro-angiogenic peptide platelet-derived growth factor (PDGF) in patients with solid tumors treated with Ang-(1-7) (Petty et al., BMC Cancer 2012; 12:404).

Tumor sections were stained with Picrosirius red to stain for collagen. As shown in FIG. 12, administration of TCAng05 reduced collagen staining. This result is similar to results observed for the native Ang(1-7) peptide, in which the native Ang-(1-7) reduced fibrosis in an orthotopic model study using mice with human breast tumors by reducing the proliferation of cancer-associated fibroblasts and their production of pro-fibrotic proteins (Cook et al., Cancer Research 2010; 70:8319-28).

These results demonstrate that oral administration of TCAng05 to mice with breast tumors reduced tumor size, by decreasing tumor cell proliferation, angiogenesis and fibrosis, as previously observed with the native Ang-(1-7).

Example 7

In Vitro Inhibition of Cancer Cell Growth by Analogs with Amino Acid Substitutions As described in Example 1, a series of TCAng05 analogs (NEP1-NEP 24) were generated with substitutions of single amino acid residues with alanine (A), by deletion of specific residues, or by substitution of key residues. The structures of analogs NEP1-NEP 24 are shown above in Table 1.

To determine whether the novel analogs reduced tumor growth, subconfluent monolayers of actively growing MDA-MB-231 human breast cancer cells in 24-well cluster plates were incubated with 100 nM of Ang(1-7) (A7), TCAng05 (TC), or one of analogs NEP1-24 for 8-10 days. Ang-(1-7) was added daily as it is rapidly degraded while the Ang(1-7) analogs were added twice weekly at the time the cells were fed. Saline was used as control (C). Cell numbers were then counted using a Nexelcom Cellometer. Assays were performed in triplicate for 2-4 replicates. As shown in FIG. 13, six of the novel analogs inhibited breast cancer cell growth similar to Ang-(1-7) or TCAng05 (circled). Both Ang-(1-7) and TCAng05 significantly reduced cell growth by 43.3±9.8% and 27.3±9.8%, respectively. Similar growth inhibition was observed with NPE4 (Ile at $R^6$ replaced with Ala), NEP12 (Ile at $R^6$ replaced with Leu), NEP8 (no -dVal-dPro), NEP16 (Nle at $R^1$ modified with an amide group ($—NH_2$) in place of an acetyl group ($—COCH_3$)), NEP20 (lysine at $R^9$ modified with a NMe moiety), and NEP24 (Dab following position $R^8$).

What is claimed is:

1. A peptide, comprising:
   (1) a compound of the formula $R^1$—Z—$R^9$—$Y^1$, wherein:
      $R^1$ is norleucine (Nle), leucine (L), alanine (A), norvaline (Nva), azidohomoalanine (Aha), or 2-Aminobutyric acid (Abu);
      Z is an amino acid sequence having at least 85% identity to SEQ ID NO:1, wherein Z has the formula $R^2$—$R^3$—$R^4$—$R^5$—$R^6$—$R^7$—$R^8$;
      $R^9$ is lysine (K), ornithine (Orn), 2,3-diaminopropionic acid (Dap), 2,4-diaminobutyric acid (Dab), or N-methyl lysine (NMe-K); and
      $Y^1$ is absent or is a single amino acid extension or a two amino acid extension attached to $R^9$;
      wherein $R^1$—Z—$R^9$ has a cyclic structure, wherein $R^1$ or $R^2$ is connected to $R^9$; or (2) SEQ ID NO:5.

2. The peptide of claim 1, wherein Z comprises one conservative amino acid substitution.

3. The peptide of claim 1, wherein Z comprises one non-conservative amino acid substitution.

4. The peptide of claim 1, wherein Z comprises one amino acid substitution in which the substitution is with alanine, phenylalanine, leucine, N-methyl tyrosine, N-methyl histidine, N-methyl isoleucine, or N-methyl valine.

5. The peptide of claim 1, wherein the peptide comprises a lactam bridge between the amino acid at position $R^2$ and the amino acid at position $R^9$.

6. The peptide of claim 1, wherein $R^1$ is modified with a —$COCH_3$ or —$NH_2$.

7. The peptide of claim 1, wherein $R^9$ is modified by —$NH_2$.

8. The peptide of claim 1, wherein $Y^1$ is D-valine (dV)-D-proline (dP), (dV), (dP), or is absent.

9. The peptide of claim 1, wherein $R^2$ is aspartic acid or alanine.

10. The peptide of claim 1, wherein $R^4$ is valine, alanine, or N-methyl valine.

11. The peptide of claim 1, wherein $R^5$ is tyrosine, N-methyl tyrosine, phenylalanine, or alanine.

12. The peptide of claim 1, wherein $R^6$ is isoleucine, N-methyl isoleucine, alanine, or leucine.

13. The peptide of claim 1, wherein $R^7$ is histidine, N-methyl histidine, or alanine.

14. The peptide of claim 1, wherein $R^8$ is proline or alanine.

15. The peptide of claim 1, wherein the peptide has an amino acid sequence selected from any one of SEQ ID NOs: 5, 6, or 8-31.

16. The peptide of claim 1, wherein the peptide has an amino acid sequence of any one of SEQ ID NOs: 5, 6, 11, 15, 23, 27, or 31.

17. The peptide of claim 1, wherein the peptide has the amino acid sequence set forth in SEQ ID NO:6.

18. The peptide of claim 1, wherein the peptide has a half life at least 100 times longer than angiotensin (1-7) in biological conditions.

19. The peptide of claim 1, wherein the peptide has an amino acid sequence of any one of SEQ ID NOs: 6, 11, 15, 23, 27, or 31.

20. A pharmaceutical composition comprising a pharmaceutically effective amount of the peptide of claim 1 and a pharmaceutically acceptable carrier.

21. The pharmaceutical composition of claim 20, wherein the pharmaceutically effective amount comprises an amount that is sufficient to inhibit cell growth or proliferation, angiogenesis, or fibrosis.

22. The pharmaceutical composition of claim 20, wherein the concentration of the peptide is in the range of 30 mg/ml to 100 mg/ml.

23. The pharmaceutical composition of claim 20, wherein the amount of the peptide is in the range of 5 mg to 1 gram.

24. A method of reducing cancer cell growth or proliferation in a subject, the method comprising administering to a subject diagnosed with a cancer an effective amount of the peptide of claim 1.

25. The method of claim 24, wherein the cancer is prostate cancer, bladder cancer, bone cancer, brain cancer, breast cancer, colon cancer, cervical cancer, endometrial cancer, fallopian tube cancer, gastrointestinal cancer, genitourinary cancer, head and neck cancer, leukemia, lung cancer, lymphoma, melanoma, liver cancer, ovarian cancer, pancreatic cancer, peritoneal cancer, prostate cancer, renal cancer, skin cancer, or testicular cancer.

26. The method of claim 24, further comprising administering a second therapeutic agent to the subject.

27. The method of claim 26, wherein the second therapeutic agent is a chemotherapeutic agent.

28. The method of claim 24, wherein a dosage of 100 mg/kg of body weight per day is administered to the subject.

29. A method of reducing angiogenesis in a cell, the method comprising administering to a subject diagnosed with a cancer an effective amount of the peptide of claim 1.

30. A method of reducing fibrosis in a tissue, the method comprising administering to a subject an effective amount of the peptide of claim 1.

* * * * *